(12) United States Patent
Harlow et al.

(10) Patent No.: US 6,177,563 B1
(45) Date of Patent: Jan. 23, 2001

(54) FLUOROALUMINATE A1F4 COMPOUNDS

(75) Inventors: Richard Leslie Harlow; Norman Herron, both of Newark, DE (US); David Lincoln Thorn, West Chester, PA (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/347,816

(22) Filed: Jul. 2, 1999

Related U.S. Application Data (62) Division of application No. 08/869,582, filed on Jun. 5, 1997, now Pat. No. 5,986,023, which is a division of application No. 08/431,212, filed on Apr. 28, 1995, now Pat. No. 5,681,953, which is a continuation-in-part of application No. 08/242,480, filed on May 13, 1994, now abandoned, which is a continuation-in-part of application No. 07/978,590, filed on Nov. 19, 1992, now abandoned.

(51) Int. Cl.$^7$ ...................................................... C07F 5/06

(52) U.S. Cl. .............................. 540/541; 546/9; 548/402; 575/370; 549/3; 549/206; 556/186

(58) Field of Search ............................... 540/541; 546/9; 548/402; 549/3, 206; 556/186

(56) References Cited

U.S. PATENT DOCUMENTS

| | | | |
|---|---|---|---|
| 2,878,240 | * 3/1959 | Schmerling | 526/99 |
| 4,034,068 | * 7/1977 | Arajmaki et al. | . |
| 4,107,080 | * 8/1978 | Taniyasu et al. | . |
| 4,396,532 | * 8/1983 | Bujadoux | . |
| 4,517,346 | * 5/1985 | Bujadoux | . |
| 4,540,841 | * 9/1985 | Miae et al. | . |
| 5,171,798 | 12/1992 | McDaniel et al. | . |
| 5,254,416 | * 10/1993 | Kubota | . |
| 5,393,509 | * 2/1995 | Corbin et al. | . |
| 5,411,584 | * 5/1995 | Akinmade et al. | . |

OTHER PUBLICATIONS

Weinland et al, *Chem. Abstracts*, 20, 719(f), 1925.
Bukovec, P et al, *Monatsh. Chem.*, 106, 483–490, 1975.
Sengupta, AK et al, *Indian J. Chem*, 17A, 107–108, 1979.
Colton, R et al, *Aust. J. Chem.*, 42, 1605–1609, 1989.
49th *Handbook of Chemistry and Physics*, C–50 and C51, 1982.
Gates, BC, *Heterogeneous Catalysis*, pp. 1–29, 1974.
Pecherz, I, et al, *J. Macromol Sci. Chem.*, A28(7), 623–532, 1991.
Iio et al., *J. of Poly Sci.* Part A, 30, 1992.
Bartsch et al, *J. of Fluor Chem*, 36, pp. 107–117, 1987.
Shreider, VA, *Chemical Abstracts*, 109, 82006n, 1988.
Gontmakher, NM et al., *Chemical Abstracts*, 103, Abstract No. 78176b, pp. 460, 1985.
Gates, BC, Catalysis by Oxide–Supported Metal Clusters, *Heterogeneous Catalysis*, pp. 1–29, 1974.

Pecherz I, Kryszewski, M, and Tracz A, The Influence of TCNQ5 Content in TCNQ Salts on Polycations with Sulfonium Groups in the Main Chain, *J. Macromol Sci. Chem.*, A28(7), pp. 623–532, 1991.
Iio et al., Synthesis of Polyallylamine Derivatives with Biguanido Groups, *Jrnl of Poly Sci.* Part A, 30, 1992.
Bartsch et al, Chlor–Fluor–Austauschreaktionen MIT Trialkyldifluor–Phosphoranen, *Jrnl of Fluor Chem*, 36, pp. 107–117, 1987.
Shreider, VA, Direct Electrochemical Synthesis of Complex Aluminum, Gallium and Indium Fluorides, *Chemical Abstracts*, 109, 82006n, 1988.
Gontmakher, NM et al., Activation of Aluminum in Fluoride–Containing Electrolytes, *Chemical Abstracts*, 103, 78176b, pp. 460, 1985.
Bukovec, P and Siftar, J, Tetramethylammonium–Flurooaluminates, –Gallates and –Indates, *Monatsh. Chem.*, 106, 483–490,1975.
Sengupta, AK and Sen K, Fluoroaluminates of Some Organic Base Cations, *Indian J. Chem.*, 17A, 107–108, 1979.
Colton, R and Eller PG, Aluminum–27 NMR Studies of Aluminium Fluoro Compleses in Dichloromethane Solution: Evidence for the Tetrafluoroaluminate Anion, *Aust. J. Chem.*, 42, 1605–1609, 1989.
Weinland et al. Chem Abs 20, 719(f) 1925.*
Bartsch, J. Flourine Chem 36, 107–117.*
Shreider Chem Abs 109, 82006n.*
Gontmakher, Chem Abs 103, 78176b (1985).*
49th CRC Handbook, pp. C–50, C–51 (1982).*
Gates in "Heterogenous Catalysis", pp. 1–29 (1984).*
Percherz, J. Macromol. Sci. Chem A28(7) pp. 623–632 (1991).*
Tio et al, J. Polymer Sci (A), 30, 2071(1992).*
Weinland, Chem Abs 20 719 (f), 1925.*
Sergupta, Ind J. Chem 17A, 107–108 (1979.*

* cited by examiner

*Primary Examiner*—Fred Zitomer (57) ABSTRACT

Fluoroaluminate compounds of formula $M^{+n}(AlF_4)_n^-$ wherein n is 1 to 3 and $M^{+n}$ is $N(R_2)_4$, $P(R_2)_4$, $As(R_2)_4$, $HN(R_2)_3$, $H_2N(R_2)_2$, $H_3N(R_2)$, $(R_2)_3P=N=P(R_2)_3$, $S[N(R_2)_2]_3$,

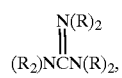

$(R_2)NCN(R_2)$, $(R)_2N-(C(R_2))_k-N(R)_3$, and $ZH_m^{+m}$ wherein Z is a base capable of accepting m protons, and various cyclic and aryl groups are disclosed as well as processes for their preparation.

5 Claims, 8 Drawing Sheets

FLUOROALUMINATE AlF4 COMPOUNDS

This is a division of application Ser. No. 08/869,582 filed Jun. 5, 1997, U.S. Pat. No. 5,986,023, which is a division of application Ser. No. 08/431,212 filed Apr. 28, 1995, U.S. Pat. No. 5,681,953, which is a continuation-in-part of application Ser. No. 08/242,480, filed May 13, 1994, now abandoned which is a continuation-in-part of application Ser. No. 07/978,590 filed Nov. 19, 1992, now abandoned.

The present invention relates to fluoroaluminate compounds and methods for their preparation.

Many compounds of the general formula $M^+AlF_4^-$ are known wherein the fluoroaluminate Al ion is six-coordinate and wherein $M^+$ is a cation, for example, wherein M is potassium, thallium, rubidium, or $NH_4$. Usually, such compounds are insoluble in nonaqueous media and have extended corner-shared fluoro-bridged network structures in the solid state.

Tetrahedrally coordinated $AlF_4^-$ compounds have been proposed to exist in a hot melt form or in vapor phase, but upon cooling reassemble into six-coordinate forms. "Tetramethylammonium-fluoroaluminates, -gallates and indates", by P. Bukovec and J. Siftar, *Monatsh. Chem.* 1975, 106, 483–490, describes the "probable" synthesis of the material $N(CH_3)_4AlF_4$ via dissolution of $AlF_3$ in aqueous HF in the presence of tetramethylammonium fluoride. The material first isolated is $N(CH_3)_4AlF_4H_2O$ which may be dehydrated at 120° C. to give a material of the noted stoichiometry. Evidence for the anhydrous tetrafluoroaluminate as containing a tetrahedral $AlF_4^-$ anion is based on the simplicity of the IR spectrum.

"Fluoroaluminates of some organic base cations" by A. K. Sengupta and K. Sen., *Indian J. Chem.*, 1979, 17A, 107–108, describes a series of preparations of fluoroaluminate salts of organic cations prepared by dissolution of aluminum hydroxide in aqueous HF in the presence of the organic cation or base. In this case a series of compounds are prepared and their chemical analyses and thermal decomposition behavior reported. The authors claim that the products of thermal decomposition of their compounds are "a mixture of aluminum fluoride and oxide". The fact that oxide is present in the final materials indicates that the materials they have prepared are in all cases mixed fluoro/aquo/hydroxo aluminate species much like the $N(CH_3)_4AlF_4H_2O$ material above.

The aqueous synthetic procedures taught in the above references are not likely to work well for many other compounds. An anhydrous process for preparation of fluoroaluminate compounds is desirable due to its versatility. Additionally, it is desirable to have compounds wherein the four-coordinate form of the $AlF_4^-$ is retained. Such materials provide low temperature routes to new phases of $AlF_3$, $AlF_3$ being a well-documented catalyst for numerous fluorocarbon transformations of industrial importance. Additionally, the solubility of such $AlF_4^-$ species in non-aqueous (organic) solvents provides a simple route for deposition onto high surface area supports for eventual conversion to well dispersed $AlF_3$ catalyst phases. The present invention provides such four-coordinate compounds, their precursors, and anhydrous processes for their preparation.

SUMMARY OF THE INVENTION

The present invention comprises a compound of the formula I, $M^{+n}(AlF_4^-)_n$ wherein $M^{+n}$ is an organic cation or polycation other than $NMe_4^+$, $NEt_4^+$, $N(n-Bu)_4^+$, guanidinium $H^+$ or PyridineH$^+$, and n is an integer from 1 to 3.

In particular the present invention comprises compounds of the above formula wherein M is selected from the group consisting of $N(R_2)_4$, $P(R_2)_4$, $AS(R_2)_4$, $HN(R_2)_3$, $H_2N(R_2)_2$, $H_3N(R_2)$, $(R_2)_3P=N=P(R_2)_3$, $S[N(R_2)_2]_3$, R is hydrogen, $C_1$–$C_{10}$ linear or branched alkyl or aryl;
$R_2$ is $C_1$–$C_{10}$ linear or branched alkyl or aryl;
n is 1; and
k is 1 to 10;
provided that $M^{+n}$ is other than $NMe_4^+$, $NEt_4^+$, $N(n-Bu)_4^+$, guanidinium $(H_2N=C(NH_2)_2)^+$ and pyridinium $(C_5H_6N)^+$.

The present invention further comprises compounds of formula I, $M^{+n}(AlF_4^-)_n$ wherein $M^{+n}$ is of the form $ZH^+$, n is 1, and Z is a base capable of accepting n protons.

The present invention further comprises anhydrous PyH$^+$ $AlF_4^-$ wherein Py is pyridine and which when thermolyzed forms pure $AlF_3$.

The present invention further comprises a polymer having a repeating unit of the formula (X) or formula (XI).

$$—(CH_2—CH_2)_m—\left(CH_2CH\atop{|\atop{NR_3^+\atop AlF_4^-}}\right)_n \quad (X)$$

$$\left(CH_2—CH\atop{|\atop C_6H_5}\right)_m—\left(CH_2CH\atop{|\atop{\phantom{X}\atop{R—\bigcirc\atop{|\atop{Q^+\atop AlF_4^-}}}}}\right)_n \quad (XI)$$

wherein
m is 0 or an integer equal to or greater than 1;
n is an integer greater than 1;
Q is NR, O, or S; and
R is H or $C_1$–$C_6$ alkyl.

The present invention further comprises processes for the preparation of compounds of formula $M^{+n}(AlF_4^-)_n$ wherein $M^{+n}$ and n are defined above. One such process comprises reacting $Al(R)_3$ with $M^{+n}(HF)_qF_n^-$ wherein M is an organic cation or polycation; n is an integer from 1 to 3; q is an integer of at least 1; and each R is independently $C_1$–$C_{12}$ alkyl, $C_1$–$C_{12}$ alkoxy, $C_1$–$C_{12}$ enolate, aryl, or $C_1$–$C_{12}$ alkamide.

A second process for the preparation of $M^{+n}(AlF_4^-)_n$ wherein n is an integer from 1 to 3, M is an organic cation of formula $ZH_n^{+n}$ and Z is a base capable of accepting n protons, comprises reacting Al(R)$_3$ wherein each R is independently $C_1$–$C_{12}$ alkyl, $C_1$–$C_{12}$ alkoxy, $C_1$–$C_{12}$ enolate, aryl, or $C_1$–$C_{12}$ alkamide with a solution of HF and Z.

A third process for the preparation of $M^{+n}(AlF_4^-)_n$ wherein $M^{+n}$ is an organic cation or polycation, and n is an integer from 1 to 3 comprises reacting $ZH_m^{+m}(AlF_4^-)_m$ with Y, wherein Z is a base capable of accepting m protons wherein m is an integer from 1 to 3, and Y is a proton-accepting base or a phosphorus ylid of formula $R_1R_2R_3P{=}CR_4R_5$ wherein $R_1$, $R_2$ and $R_3$ are each independently linear, branched or cyclic $C_1$–$C_{10}$ alkyl or substituted $C_1$–$C_{10}$ alkyl, $C_1$–$C_{10}$ alkoxy, aryl, aryloxy, heterocyclic, substituted heterocyclic, or together two or more of $R_1$, $R_2$ or $R_3$ may form a ring of 3 to 10 atoms; $R_4$ and $R_5$ are each independently hydrogen, linear, branched or cyclic $C_1$–$C_{10}$ alkyl or substituted alkyl, $C_1$–$C_{10}$ alkoxy, aryl, aryloxy, heterocyclic, substituted heterocyclic or $R_4$ and $R_5$ together may form a ring of 3 to 10 atoms.

A fourth process for the preparation of $M^{+n}(AlF_4^-)_n$ wherein $M^{+n}$ is an organic cation or polycation, and n is an integer from 1 to 3 comprises reacting $ZH_m^{+m}(AlF_4^-)_m$, wherein Z is a base capable of accepting m protons wherein m is an integer from 1 to 3, with $M^{+n}(X^-)_n$ wherein M is an organic cation or polycation other than $H^+$ and X is a stronger base than Z.

A fifth process for the preparation of $M^{+n}(AlF_4^-)_n$ wherein $M^{+n}$ is an organic cation or polycation, and n is an integer from 1 to 3 comprises reacting $ZH_m^{+m}(AlF_4^-)_m$, wherein Z is a base capable of accepting m protons wherein m is an integer from 1 to 3, with $M^{+n}(X^-)_n$ wherein $M^{+n}$ is an organic cation or polycation other than $H^+$ and $X^-$ is an anion which forms a compound $ZH_m^{+m}(X^-)_m$ easily separable from the $M^{+n}(AlF_4^-)_n$ product.

DETAILED DESCRIPTION OF THE INVENTION

The present invention comprises compounds of formula I $$M^{+n}(AlF_4^-)_n \qquad (I)$$

wherein $M^{+n}$ is an organic cation or polycation other than $NMe_4^+$, $NEt_4^+$, $N(n\text{-}Bu)_4^+$, guanidinium $H^+$, or PyridineH$^+$, and n is an integer from 1 to 3. In particular the present invention includes compounds of formula I wherein M is selected from the group consisting of $N(R_2)_4$, $P(R_2)_4$, $As(R_2)_4$, $HN(R_2)_3$, $H_2N(R_2)_2$, $H_3N(R_2)$, $(R_2)_3P{=}N{=}P(R_2)_3$, $S[N(R_2)_2]_3$, R is hydrogen, $C_1$–$C_{10}$ linear or branched alkyl or aryl;
$R_2$ is $C_1$–$C_{10}$ linear or branched alkyl or aryl;
n is 1; and
k is 1 to 10;
provided that $M^{+n}$ is other than $NMe_4^+$, $NEt_4^+$, $N(n\text{-}Bu)_4^+$, guanidinium $(H_2N{=}C(NH_2)_2)^+$ and pyridinium $(C_5H_6N)^+$.

The present invention further comprises compounds of the formula I, $M^{+n}(AlF_4^-)_n$ wherein $M^{+n}$ is of the form $ZH_m^{+m}$, n is 1, m is an integer of 1 to 3, and Z is a base capable of accepting m protons.

The present invention further comprises $PyH^+AlF_4^-$ wherein Py is pyridine and which when thermolyzed forms pure $AlF_3$.

In the above recitations and the processes of the present invention, the term "alkyl" denotes straight chain or branched alkyl; e.g., methyl, ethyl, n-propyl, i-propyl, or the different butyl, pentyl, hexyl, etc. isomers. Cyclic alkyls include cyclopropyl, cyclobutyl, cyclopentyl, cyclohexyl, etc. The abbreviation Me denotes methyl, Et denotes ethyl, and n–Bu denotes n-butyl.

"Alkenyl" denotes straight chain or branched alkenes; e.g., 1-propenyl, 2-propenyl, and the different butenyl, pentenyl, hexenyl, etc. isomers. "Dienyl" denotes polyenes having two double bonds such as 1,3-hexadiene and the like.

"Alkoxy" denotes methoxy, ethoxy, n-propyloxy, isopropyloxy and the different butoxy, pentoxy, hexyloxy, etc. isomers.

"Aryl" includes aromatic hydrocarbons such as benzene, substituted benzene, such as toluene, aniline, benzoic acid, halobenzene, nitrobenzene, etc., naphthalene, or substituted naphthalene.

"Heterocyclic" denotes 5- or 6-membered rings containing 1 to 3 nitrogen, oxygen, or sulfur atoms or combinations thereof such as furanyl, thiofuranyl, tetrahydrofuranyl, thiopheneyl, pyrrolyl, pyrazolyl, triazolyl, dithiolyl, oxathiolyl, oxazolyl, thiazolyl, dioxazolyl, oxathiazolyl, pyranyl, pyronyl, pyridinyl, pyrimindinyl, pyrazinyl, triazinyl, oxazinyl, oxathiazinyl, imidazolyl, etc. Preferred in the compounds and processes of the present invention are pyridinyl, furanyl, tetrahydrofuranyl, pyranyl, imidazolyl or thiopheneyl.

Substituted alkyl includes $C_1$–$C_{10}$ alkyl having at least one substituent. Suitable substituents include hydrogen, $C_1$–$C_{10}$ alkyl, $C_2$–$C_{10}$ alkenyl, $C_2$–$C_{10}$ alkynyl, or aryl.

Substituted heterocyclic includes heterocyclic as defined above having at least one substituent. Suitable substituents include hydrogen, $C_1$–$C_{10}$ alkyl, $C_2$–$C_{10}$ alkenyl, $C_2$–$C_{10}$ alkynyl, or halogen.

"Polycation" denotes multiple singly charge atoms linked to form a cation having a net charge greater than one. It is not meant to indicate multiple charges on individual atoms making up the cation.

Preferred cations include trialkylammonium, tetraalkylammonium wherein alkyl is other than methyl, ethyl and butyl, tetraalkylphosphonium and mixed alkyl- and arylphosphonium where the P atom is bound to four different carbon atoms, and analogous arsonium compounds. Also preferred in addition to the above are pyrilium and substituted pyrilium, thiopyrilium and substituted thiopyrilium, and bis(triphenylphosphine)-iminium cations, as well as polyvinylpyridinium and polyalkyleneammonium polycations.

Preferred compounds are: triphenylmethylphosphonium tetrafluoroaluminate, tetraethylphosphonium tetrafluoroaluminate, tetraphenylphosphonium tetrafluoroaluminate, tetraphenylarsonium tetrafluoroaluminate, tetrapropylammonium tetrafluoroaluminate or 1,8-bisdimethylaminonapthalenium tetrafluoroaluminate.

The present invention also comprises compounds of formula $M^{+n}(AlF_4^-)_n$ wherein $M^{+n}$ is of the form $ZH_n^{+n}$ wherein n is 1 and wherein Z is a base capable of accepting n protons, preferably amine, pyridine or ylid. Preferred are such compounds wherein Z is pyridine, 1,8-bis(dimethylamino)naphthalene, 2,4,6-trimethylpyridine (collidine), or 2,6-dimethylpyridine (lutidine). Also preferred is anhydrous $PyH^+AlF_4^-$ wherein Py is pyridine and which when thermolyzed at a temperature of from about 285° C. to about 450° C. forms pure $AlF_3$. Pure is used herein to mean that the $AlF_3$ is uncontaminated with $Al_2O_3$ as detectable by X-ray diffraction.

The compounds of formula I can be prepared as described below in rigorously pure and anhydrous form. Depending upon the choice of $M^{+n}$, the compounds may be freely soluble in nonaqueous solvents, and the $AlF_4^-$ anion may be four-coordinate with no bridging fluorides nor additional ligating groups.

The compounds of formula I are useful for the preparation of pure $AlF_3$ in several of its crystalline phases such as alpha, beta, eta, theta, or kappa, without oxide or hydroxide contamination or incorporation. $AlF_3$ results from the anhydrous thermal decomposition of compounds of formula. I at temperatures ranging from about 285° C. to about 450° C. depending upon the exact composition of the organic cation or polycation. A. K. Sengupta and K. Sen (Indian J. Chem. 1979, 17A, 107–108) briefly describe the thermolysis of several fluoroaluminate salts of organic cations to "a mixture of aluminum fluoride and oxide", the oxide arising from water or hydroxide present in their "fluoroaluminate" materials. Bulk $AlF_3$ is useful as a solid-state catalyst for chlorofluorocarbon isomerization and fluorination, and high surface area $AlF_3$ dispersed onto carbon, organic, or inorganic supports may be a useful catalyst for these or other reactions. Embodiments of the latter are described by U.S. Pat. No. 5,171,798 issued Dec. 15, 1992 to McDaniel et al., wherein fluoroaluminum species generated on a support of alumina were subsequently treated with e.g., chromium to obtain active olefin polymerization catalysts. Routes to such high surface area $AlF_3$ phases dispersed on inorganic supports are provided by the solubility of $AlF_4^-$ species of the formula I type in non-aqueous solvents. Suitable non-aqueous solvents include solvents such as methanol, ethanol, pyridine, acetonitrile, acetone, tetrahydrofuran, dimethylsulfoxide, dimethylformamide, formamide, dichloromethane or chloroform. The $AlF_4^-$ species are readily deposited onto high surface area supports and subsequent thermolysis converts the $AlF_4^-$ species to well-dispersed $AlF_3$ phases.

The present invention further comprises a polymer comprising repeating units having the formulae (X) or (XI)

(X)

(XI)

wherein m is 0 or an integer equal to or greater than 1; n is an integer greater than 1; Q is NR, O or S; and R is H or $C_1$–$C_6$ alkyl. Preferred polymers are polyethylene containing pendant quaternary ammonium groups and polystyrene containing occasional incorporated polyvinyl pyridinium groups. The polymers of the present invention are prepared by anion exchange reactions known to those skilled in the art.

In a preferred example, a commercially available anion exchange resin in its halide ($X^-$ where X=Cl, Br, I) form may be packed in a vertical chromatography column using methanol solvent. A solution of collidineH$^+$ $AlF_4^-$ in methanol may be added to the top of the column and the solution drained through the column. As the $AlF_4^-$ solution travels through the column it will displace the original halide ion ($X^-$) from the anion exchange resin so that the column eluent will consist of collidineH$^+X^-$ while the column will become transformed to the desired $AlF_4^-$ form. The progress of this transformation may be monitored by analyzing the effluent for halide ion ($X^-$). When no further halide is present the exchange of $AlF_4^-$ for $X^-$ on the resin is complete generating polymers of repeating units of formula (X) or (XI).

The utility of the $AlF_4^-$ exchanged resin is in its ability to be transformed into the corresponding $AlF_3$ phase upon mild thermal treatment (300–400° C.) in an inert atmosphere (nitrogen, argon, helium or vacuum) to eliminate RF (where R is H or alkyl or aryl originating from the resin). The resulting composite material of $AlF_3$ dispersed on an organic polymeric resin is useful as a high surface area form of the known fluorocarbon transformation catalyst $AlF_3$.

The present invention further comprises the processes of Equations 1 to 5 useful for the preparation of compounds of formula I as shown in Scheme 1.

Scheme 1

(Equation 1)

(Equation 2)

(Equation 3)

(Equation 4)

$n/m[((ZH)_m^{+m})(AlF_4^-)_m] + M^{+n}(X^-)_n \rightarrow$  (Equation 5)

$M^{+n}(AlF_4^-)_n + n/m((ZH)_m^{+m})(X^-)_m$

In Equation 1 an aluminum source, $Al(R)_3$, wherein each R is independently $C_1$–$C_{12}$ alkyl, $C_1$–$C_{12}$ alkoxy, $C_1$–$C_{12}$ enolate, aryl, or $C_1$–$C_{12}$ alkamide is reacted with $M^{+n}(HF)_qF_n^-$ wherein $M^{+n}$ is an organic cation or polycation as defined in formula I, q is greater than or equal to 1, and n is an integer from 1 to 3. Such starting materials can be made according to the procedures of Colton, R., et al. Aust. J. Chem. 42, 1605–9, 1989. The reaction is conducted in a solvent which is unreactive with $Al(R)_3$ or which undergoes only coordination to $Al(R)_3$ such as ethers, tertiary amines, or nitrogen-containing heterocyclic compounds. Preferred is pyridine. The mole ratio of $Al(R)_3$ to q in $M^{+n}(HF)_qF_n^-$ is at least 1:3. The reaction is conducted at a temperature of from about –100° C. to about 150° C. depending upon the solvent employed. Preferably the reaction is conducted at a temperature of from about –40° C. to 60° C. Use of an inert atmosphere such as nitrogen or argon is required to exclude oxygen and water. The reaction is conducted at ambient pressure or under a vacuum. The preferred pressure is from about 0.01 to 5 atm ($10^3$ to $5 \times 10^5$ Pa). Agitation is optional but preferred. The desired product, $M^{+n}(AlF_4^-)_n$ can be isolated using routine procedures such as filtration or crystallization.

For the process of Equation 2, an aluminum source $Al(R)_3$, wherein each R is independently $C_1$–$C_{12}$ alkyl, $C_1$–$C_{12}$ alkoxy, $C_1$–$C_{12}$ enolate, aryl or $C_1$–$C_{12}$ alkamide, such as trimethylaluminum is mixed with reagent Z, under an inert atmosphere and anhydrous HF added. Z is a base capable of accepting n protons wherein n is an integer from 1 to 3. Such starting materials are commercially available or are prepared according to Colton above. Examples of suitable reagent Z include pyridine, triethylamine, substituted pyridines and substituted amines. The mole ratio of $Al(R)_3$ to HF employed is at least about 1:4. Suitable solvents include amines, phosphines, arsines, nitrogen containing heterocyclic compounds or Z as defined above. Preferred for use in this process are pyridine, substituted pyridine or trialkylamines. The reaction is conducted at a temperature of from about –100° C. to about 150° C., preferably at –40° C. to 60° C. depending upon the solvent used. Use of ambient pressure or a vacuum is employed, preferably from about 0.01 to 5 atm ($10^3$ to $5 \times 10^5$ Pa).

An inert atmosphere such as nitrogen, argon, or helium is employed to maintain an environment free of oxygen, water or carbon dioxide. Agitation is optional but preferred. After stirring, the reaction mixture is left to stand at ambient temperature and the desired $ZH_m^{+m}(AlF_4^-)_m$ product may precipitate out and can be isolated by filtration or other equivalent means.

$ZH_m^{+m}(AlF_4^-)_m$, prepared as in the process of Equation 2, can be employed in the process of Equation 3. The Equation 3 process comprises reacting $ZH_m^{+m}(AlF_4^-)_m$ with Y, wherein Z is a base capable of accepting m protons wherein m is an integer from 1 to 3, and Y is a base capable of accepting n protons wherein n is an integer from 1 to 3 or a phosphorus ylid, and Y is more basic than Z. In Equation 3, Y is a proton-accepting base such as pyridine, amine, or a phosphorus ylid of formula $R_1R_2R_3P=CR_4R_5$ wherein $R_1$ $R_2$ and $R_3$ are each independently linear, branched or cyclic $C_1$–$C_{10}$ alkyl or substituted $C_1$–$C_{10}$ alkyl, alkylene, $C_1$–$C_{10}$ alkoxy, aryl, aryloxy, heterocyclic, substituted heterocyclic, or together two or more of $R_1$, $R_2$ or $R_3$ may form a ring of 3 to 10 atoms;

$R_4$ and $R_5$ are each independently hydrogen, linear, branched or cyclic $C_1$–$C_{10}$ alkyl or substituted $C_1$–$C_{10}$ alkyl, alkylene, $C_1$–$C_{10}$ alkoxy, aryl, aryloxy, heterocyclic, substituted heterocyclic or $R_4$ and $R_5$ together may form a ring of 3 to 10 atoms; and Y is a stronger base than Z.

Substituted alkyl, heterocyclic, and substituted heterocyclic are as previously defined.

Examples of suitable Z include pyridine, 2,4,6-trimethylpyridine, 1,8-bis(dimethylamino)naphthalene, 2,6-dimethylpyridine and the like. The mole ratio of Y to $ZH_m^{+m}(AlF_4^-)_m$ employed is m, wherein m is an integer of 1 to 3 or greater. Suitable solvents include chlorocarbons, ethers, amines, nitrogen-containing heterocyclic compounds or Y as defined above. Preferred solvents are tetrahydrofuran and substituted pyridines. The reaction is conducted at a temperature of from about –100° C. to about 150° C., preferably from about –40° C. to 60° C. depending upon the solvent employed. Exclusion of water vapor, oxygen and carbon dioxide is required if they would react with Y or Z. Use of an inert atmosphere such as nitrogen, argon or helium is preferred. The reaction is conducted at ambient pressure or under vacuum, preferably from about 0.01 to 5 atm ($10^3$ to $5 \times 10^5$ Pa). Use of vigorous agitation is preferred.

It has been found that it is particularly advantageous to use bases as reagent Y in Equation 3 such that their conjugate acids $YH^+$ are incapable of forming strong hydrogen bonds to the fluoroaluminate anion, as the resulting compounds $YH^+AlF_4^-$ then tend to be freely soluble in organic solvents. Two particular examples are 1,8-bis (dimethylamino)naphthalene where the conjugate acid, even though possessing NH groups, is a very weak hydrogen-bonding participant; and $(C_2H_5)_3P=CHCH_3$, where the conjugate acid has hydrogen only bonded to carbon and does not normally participate in hydrogen-bonding. Most ylid compounds of phosphorus, arsenic, sulfur, nitrogen, and other elements are suitable to serve as base Y in Equation 3 and likewise provide conjugate acid cations $YH^+$ that form only weak hydrogen bonds to fluoroaluminate anions.

A further process for the preparation of $M^{+n}(AlF_4^-)_n$ is the reaction of Equation 4. $ZH_m^{+m}(AlF_4^-)_m$, prepared as in Equation 2, wherein Z is a base capable of accepting m protons wherein m is an integer of 1 to 3, is reacted in a simple ion metathesis with $M^{+n}(X^-)_n$ wherein $M^{+n}$ is an organic cation or polycation as defined in formula I and $X^-$ is a stronger base than Z. Suitable cations for $M^+$ include, for example, $As(C_6H_5)_4^+$, $P(C_6H_5)_4^+$, $P(C_6H_5)_3CH_3^+$, $N(C_2H_5)_4^+$ and the like. Suitable anions for $X^+$ include 2,6-dimethylphenolate, trimethylacetate, and the like. The mole ratio of $M^{+n}(X^-)_n$ to $ZH_m^{+m}(AlF_4^-)_m$ is preferably m:n. An excess of either can be used. The reaction is conducted in a solvent such as a halocarbon, ether, alcohol, ketone, amine, or heterocyclic nitrogen compound. Preferred solvents are tetrahydrofuran, methanol, acetone, dichloromethane, or pyridine. The temperature employed depends upon the solvent used and can range from about −100° C. to about 150° C., preferably −40° C. to 60° C. The pressure employed can be ambient or a vacuum used, and is preferably from about 0.01 to about 5 atm ($10^3$ to $5 \times 10^5$ Pa). Water vapor should be excluded so the reaction is conducted in an inert atmosphere such as nitrogen, argon, or helium. The desired product, $M^{+n}(AlF_4^-)_n$ is isolated by conventional means such as crystallization or filtration.

A further process for the preparation of $M^{+n}(AlF_4^-)_n$ is the reaction of Equation 5 comprising reacting $ZH_m^{+m}(AlF_4^-)_m$ wherein Z is a base capable of accepting m protons wherein m is an integer of 1 to 3, with $M^{+n}(X^-)_n$ wherein $M^{+n}$ is an organic cation or polycation as defined in formula I and $X^-$ is a halide or other anion, such as $SCN^-$, $N_3^-$, $OCN^-$, $CF_3SO_3^-$, $ClO_4^-$, $NO_3^-$, or $SO_4^{2-}$. The reaction conditions are substantially the same as those described for Equation 4 except that $X^-$ is not a stronger base than Z, but can be of comparable or lesser strength.

The following examples are representative of the present invention. The desired product, $M^{+n}(AlF_4^-)_n$, is isolated by conventional means such as crystallization or filtration.

EXAMPLE 1

Preparation of H-pyridine$^+$ AlF$_4^-$

Figure 1:
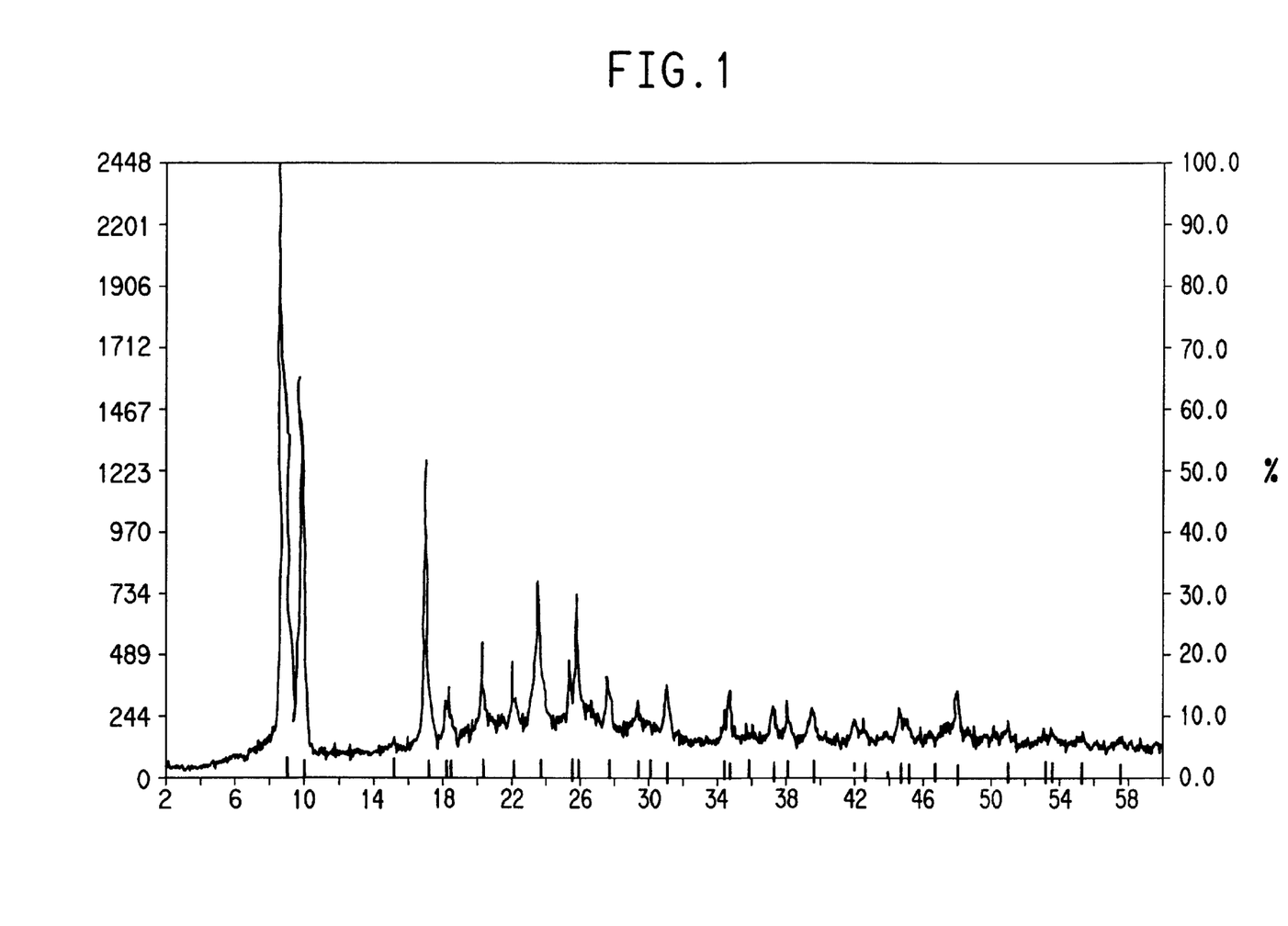
FIG. 1 depicts the powder X-ray diffraction pattern of $M^{+n}(AlF_4^-)_n$ wherein $M^{+n}$ is H-pyridine and n is 1.

Under an $N_2$ atmosphere in a drybox, 0.216 g trimethylaluminum (CAUTION! This material is pyrophoric in air and reacts vigorously with many solvents, including alcohols, ethers, and pyridine) was dissolved in 20 mL dry pyridine in a plastic beaker. To this solution was added 0.37 g of HF-pyridine solution (separately determined to have the approximate composition HF(pyridine)$_{0.135}$, equivalent weight 30.7). After the vigorous reaction had subsided the mixture was stirred for 1 hour. Additional pyridine (20 mL) was added and the mixture was transferred to a glass vessel. After standing 3 days at ambient temperature the mixture was filtered and the insolubles dried in vacuum at ambient temperature, yield 0.39 g. The resulting material contained excess solvent. Anal. Calcd. for H (pyridine)$_{1.3}$AlF$_4$: C, 37.75%; H, 3.65%; N, 8.80%. Found (Galbraith): C, 37.77, 37.37%; H, 3.57, 3.67%; N, 8.47, 8.69%. The X-ray powder diffraction pattern of a typical sample is shown in FIG. 1. The corresponding data is in Table I.

TABLE I

| Generator Settings | 40 kv, 30 mA |
|---|---|
| CU alpha1,2 wavelengths | 1.540598, 1.544435 Ang |
| Step size, sample time | 0.20 deg, 0.50 s, 25.00 s/deg |
| Monochromator used | Yes |
| Divergence slit | Automatic (specimen length: 12.5 mm) |
| Analysis program number | 1 |
| Peak angle range | 2.000–60.000 deg |
| Peak position criterion | Top of smoothed data |
| Number of peaks in file | 33 (Alpha1: 33, Amorphous: 0) |

| Peak No. | Angle (deg) | Width (deg) | Peak (cts) | Backg (cts) | D spac (Ang) | I/Imax (%) |
|---|---|---|---|---|---|---|
| 1 | 2.272 | 0.24 | 22 | 27 | 38.8774 | 1 |
| 2 | 9.283 | 0.28 | 2343 | 99 | 9.5276 | 100 |
| 3 | 10.258 | 0.14 | 1459 | 93 | 8.6240 | 62 |

TABLE I-continued

| Generator Settings | 40 kv, 30 mA |
|---|---|
| CU alpha1,2 wavelengths | 1.540598, 1.544435 Ang |
| Step size, sample time | 0.20 deg, 0.50 s, 25.00 s/deg |
| Monochromator used | Yes |
| Divergence slit | Automatic (specimen length: 12.5 mm) |
| Analysis program number | 1 |
| Peak angle range | 2.000–60.000 deg |
| Peak position criterion | Top of smoothed data |
| Number of peaks in file | 33 (Alpha1: 33, Amorphous: 0) |

| Peak No. | Angle (deg) | Width (deg) | Peak (cts) | Backg (cts) | D spac (Ang) | I/Imax (%) |
|---|---|---|---|---|---|---|
| 4 | 15.422 | 0.20 | 64 | 82 | 5.7455 | 3 |
| 5 | 17.372 | 0.16 | 1129 | 87 | 5.1048 | 48 |
| 6 | 18.445 | 0.08 | 219 | 89 | 4.8103 | 9 |
| 7 | 18.715 | 0.14 | 262 | 89 | 4.7415 | 11 |
| 8 | 20.630 | 0.10 | 408 | 95 | 4.3055 | 17 |
| 9 | 22.357 | 0.18 | 353 | 99 | 3.9766 | 15 |
| 10 | 23.872 | 0.20 | 645 | 103 | 3.7275 | 28 |
| 11 | 25.650 | 0.06 | 339 | 107 | 3.4731 | 14 |
| 12 | 26.057 | 0.14 | 581 | 109 | 3.4197 | 25 |
| 13 | 27.780 | 0.08 | 289 | 113 | 3.2115 | 12 |
| 14 | 29.455 | 0.12 | 161 | 118 | 3.0325 | 7 |
| 15 | 30.117 | 0.20 | 102 | 118 | 2.9673 | 4 |
| 16 | 31.105 | 0.10 | 231 | 122 | 2.8753 | 10 |
| 17 | 34.410 | 0.06 | 112 | 129 | 2.6064 | 5 |
| 18 | 34.745 | 0.20 | 207 | 129 | 2.5820 | 9 |
| 19 | 35.878 | 0.48 | 48 | 129 | 2.5030 | 2 |
| 20 | 37.275 | 0.24 | 137 | 129 | 2.4124 | 6 |
| 21 | 38.048 | 0.08 | 159 | 129 | 2.3651 | 7 |
| 22 | 39.627 | 0.20 | 119 | 129 | 2.2744 | 5 |
| 23 | 41.950 | 0.16 | 98 | 129 | 2.1537 | 4 |
| 24 | 42.610 | 0.24 | 66 | 129 | 2.1219 | 3 |
| 25 | 44.735 | 0.12 | 135 | 143 | 2.0259 | 6 |
| 26 | 45.190 | 0.20 | 77 | 148 | 2.0065 | 3 |
| 27 | 46.768 | 0.10 | 27 | 148 | 1.9425 | 1 |
| 28 | 48.055 | 0.12 | 196 | 145 | 1.8934 | 8 |
| 29 | 51.140 | 0.24 | 56 | 148 | 1.7862 | 2 |
| 30 | 53.180 | 0.12 | 48 | 133 | 1.7224 | 2 |
| 31 | 53.658 | 0.24 | 45 | 133 | 1.7082 | 2 |
| 32 | 55.320 | 0.64 | 24 | 130 | 1.6607 | 1 |
| 33 | 57.472 | 0.24 | 25 | 1274 | 1.6035 | 1 |

EXAMPLE 2

Preparation of BH$^+$AlF$_4^-$, B=1,8-bis (dimethylamino)naphthalene

Figure 2:
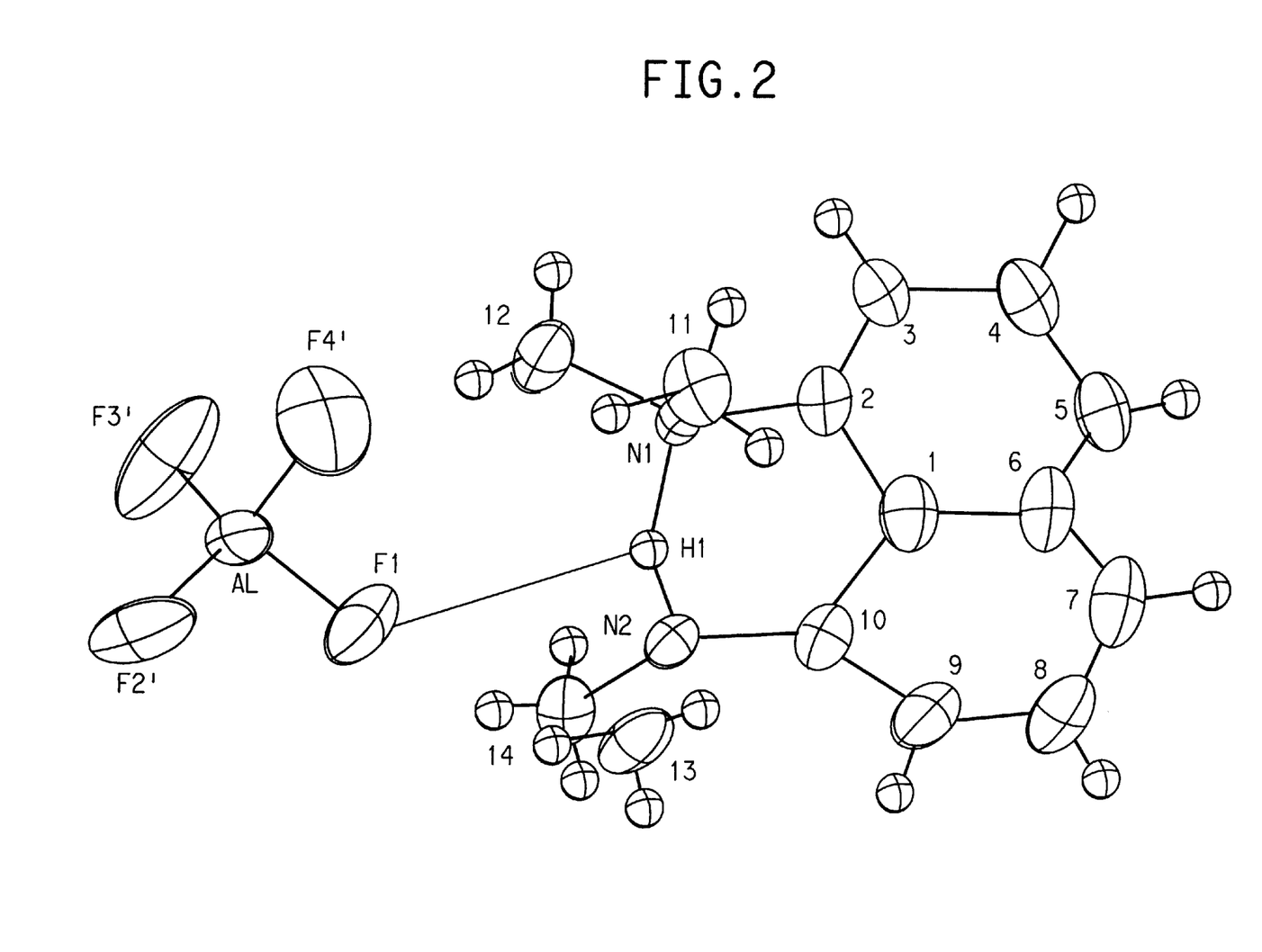
FIG. 2 depicts the X-ray crystal structure of $ZH^+AlF_4^-$ wherein Z is 1,8-bis(dimethylamino)naphthalene.

H-pyridine$^+$AlF$_4^-$ (0.19 g) prepared as in Example 1 and 1,8-bis(dimethylamino)naphthalene (0.21 g) were combined in a ca. 2 mL dry acetonitrile, under nitrogen in a drybox. The mixture was stirred and rapidly became a solution. Diethyl ether was then slowly added until precipitation began, at which time the mixture was filtered and the initial precipitate was discarded. More diethyl ether was added to the solution, eventually precipitating 0.19 g white solid, mp. 260° C. Anal. Calcd. for $C_{14}H_{19}N_2Al_1F_4$: C, 52.83%; H, 6.02%; N, 8.80%; Al, 8.48%; F, 23.88%. Found (Galbraith): C, 52.61, 52.87%, H, 6.06, 5.78%; N, 8.74, 8.80%; Al 8.73, 8.40%; F, 18.79, 18.70%. The fluorine analysis is poor owing perhaps to incomplete degradation of AlF$_4^-$ during the analytical procedure. IR (Nujol) AlF$_4^-$ at 790/cm. NMR (0.002 M in CD$_3$CN): $^{19}$F, −194.2 ppm, 6 lines, J=38 Hz; $^{27}$Al, 49.2 ppm, binomial quintet, J=38 Hz. A single crystal, grown from CH$_2$Cl$_2$/toluene solution, was used for an X-ray structure determination. The resulting data shown in Table II and FIG. 2.

The X-ray crystal analysis was as follows:

CRYSTAL DATA $AlF_4N_2C_{14}H_{19}$, from $CH_2Cl_2$/toluene, colorless, square plate, ~0.34×0.10×0.54 mm, triclinic, $P\bar{1}$ (No. 2), a=8.081(1), b=8.307(1), c=12.375(1)Å, α=82.84(1), β=76.16(1), γ=79.13(1)°, from 47 reflections, T=−100° C., V=789.4Å$^3$, Z=2, FW=318.30, Dc=1.339 g/cc, $\mu$(Mo)=1.58 cm$^{-1}$.

DATA COLLECTION AND TREATMENT

Syntex $R_3$ diffractometer, MoKa radiation, 7858 data collected, 5.0°≦2θ≦55.0°, maximum h,k,l=10 10 31, data octants =+++, ++−, +−+, +−−, −++, −+−, ω scan method, scan width=1.50°ω, scan speed=3.90–11.70°/min., typical half-height peak width=0.70°ω, 6.1% variation in azimuthal scan, no absorption correction, 1981 unique reflections with I≧3.0 σ(I).

SOLUTION AND REFINEMENT

Structure solved by direct methods (SHELXS), refinement by full-matrix least squares on F. scattering factors from Int. Tables for X-ray Crystallography, Vol. IV, including anomalous terms for Al, biweight $[\sigma^2(1)+0.0009I^2]^{-\frac{1}{2}}$, (excluded 2), refined anisotropic: all non-hydrogen atoms, isotropic: H, 293 parameters, data/parameter ratio=6.75, final R=0.051, Rw=0.048, error of fit=1.70, max Δ/σ=0.12, largest residual density=0.27e/Å$^3$, near F1.

RESULTS

The proposed crystal structure with an isolated, monomeric $AlF_4$ anion was confirmed even though the anion was two-fold disordered around the Al(1)—F(1) axis. F(1) was fully occupied: the remainder of the fluorines were assigned occupancies of 0.5. F(1) was also unique in that it formed the closest contact with the proton, H(1). The distance, 2.77 Å, was too long to be considered a real hydrogen bond, the approach of the anion to the proton being hindered by the cluster of methyl groups. All of the hydrogen atoms were refined. Crystals of this compound were invariably twinned. The crystal selected for this study had a single set of diffraction spots when photographed but generally had broad omega scans and some split peaks. In addition, one low-angle peak had sufficient intensity to suggest that the cell should be doubled. The cell was doubled during the data collection but no other reflections with significant intensity were found. The intensity was probably diffuse scattering related to the disordered anion.

TABLE II

Fractional Coordinates (X10000) and Isotropic Thermal Parameters

| ATOM | X | Y | Z | BISO |
|---|---|---|---|---|
| Al(1) | 3342.8(11) | 2601.4(12) | −1791.2(7) | 3.1(1)' |
| F(1) | 3543(3) | 2960(3) | −553(2) | 7.8(1)' |
| F(2') | 5040(8) | 2716(12) | −2673(5) | 9.9(3)' |
| F(2") | 4929(9) | 1435(10) | −2592(6) | 10.7(3)' |
| F(3') | 1658(8) | 3708(9) | −2083(4) | 8.0(2)' |
| F(3") | 3303(14) | 4424(6) | −2490(5) | 11.1(3)' |
| F(4') | 2895(11) | 730(6) | −1519(5) | 9.5(3)' |
| F(4") | 1617(8) | 1967(15) | −1797(5) | 11.1(4)' |
| N(1) | 685(3) | 1749(3) | 1764(2) | 2.5(1)' |

TABLE II-continued

Fractional Coordinates (X10000) and Isotropic Thermal Parameters

| ATOM | X | Y | Z | BISO |
|---|---|---|---|---|
| N(2) | 2896(3) | 3451(3) | 2033(2) | 3.0(1)' |
| C(1) | 701(4) | 2507(3) | 3632(2) | 2.9(1)' |
| C(2) | −153(3) | 1845(3) | 2948(2) | 2.7(1)' |
| C(3) | −1658(4) | 1258(4) | 3389(3) | 3.6(1)' |
| C(4) | −2423(5) | 1314(4) | 4540(3) | 4.3(1)' |
| C(5) | −1621(5) | 1876(4) | 5215(3) | 4.2(1)' |
| C(6) | −42(4) | 2459(3) | 4801(2) | 3.5(1)' |
| C(7) | 822(5) | 3008(4) | 5518(3) | 4.4(1)' |
| C(8) | 2309(6) | 3604(4) | 5118(3) | 4.8(1)' |
| C(9) | 3014(5) | 3752(4) | 3966(3) | 4.0(1)' |
| C(10) | 2228(4) | 3227(3) | 3244(2) | 3.1(1)' |
| C(11) | 1549(5) | 51(4) | 1523(3) | 4.1(1)' |
| C(12) | −489(4) | 2437(5) | 1009(3) | 3.8(1)' |
| C(13) | 4765(4) | 2773(6) | 1683(3) | 4.8(1)' |
| C(14) | 2492(6) | 5191(5) | 1603(3) | 4.2(1)' |
| H(1) | 1966(50) | 2654(48) | 1695(31) | 8.8(11) |
| H(3) | −2157(35) | 780(34) | 2909(23) | 3.6(7) |
| H(4) | −3618(45) | 868(41) | 4811(27) | 6.0(8) |
| H(5) | −2161(41) | 1907(39) | 6003(29) | 5.4(8) |
| H(7) | 311(44) | 2861(43) | 6298(31) | 6.3(9) |
| H(8) | 2776(41) | 3998(39) | 5551(28) | 5.1(8) |
| H(9) | 3974(38) | 4289(37) | 3662(24) | 4.0(7) |
| H(11) | 2133(37) | 44(34) | 798(26) | 3.4(7) |
| H(11') | 645(38) | −691(38) | 1635(23) | 4.3(7) |
| H(11") | 2436(46) | −263(44) | 1961(29) | 5.8(9) |
| H(12) | 166(37) | 2520(33) | 297(25) | 3.5(7) |
| H(12') | −1083(44) | 3591(46) | 1185(27) | 5.7(9) |
| H(12") | −1400(42) | 1808(38) | 1040(24) | 4.7(8) |
| H(13) | 5075(36) | 2801(35) | 861(28) | 4.3(7) |
| H(13') | 4958(43) | 1536(48) | 2056(29) | 5.9(9) |
| H(13") | 5354(42) | 3399(40) | 1957(27) | 5.3(8) |
| H(14) | 2892(37) | 5222(35) | 817(27) | 4.2(7) |
| H(14') | 3008(43) | 5898(44) | 1939(28) | 5.8(9) |
| H(14") | 1199(49) | 5607(41) | 1826(28) | 5.5(9) |

EXAMPLE 3

Preparation of CollidineH$^+$ $AlF_4^-$

Figure 3A:
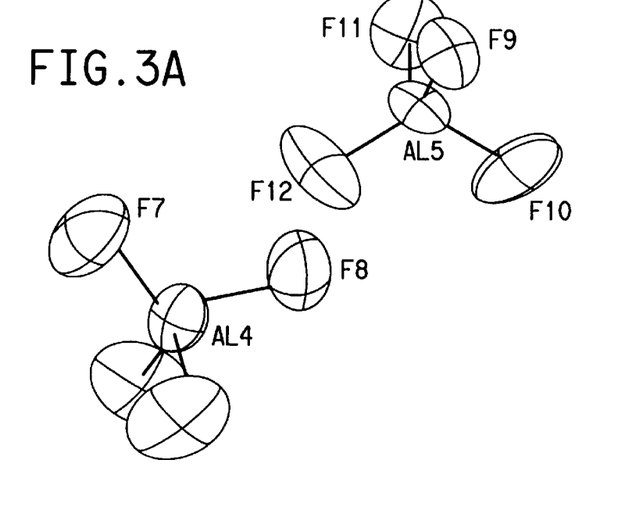
FIG. 3a depicts the structure of the tetrahedral $AlF_4^-$ anion as obtained from the x-ray crystal structure of collidinium $AlF_4$.
Figure 3B:
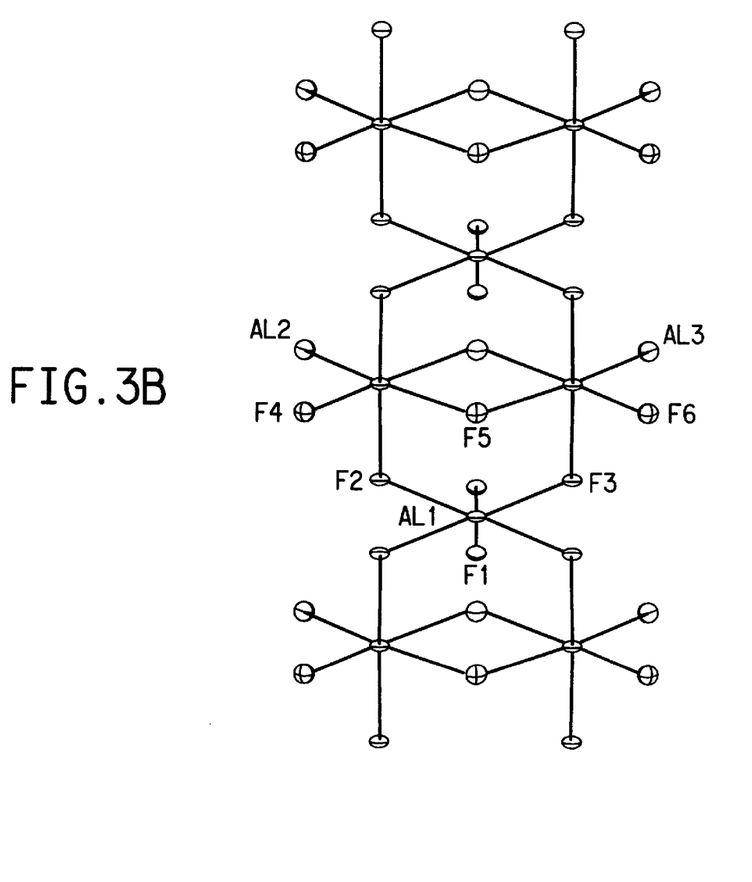
FIG. 3b depicts the structure of a chain of octahedral $AlF_6$ units linked through corner and edge sharing of F as obtained from the x-ray crystal structure of collidinium $AlF_4$.
Figure 3C:
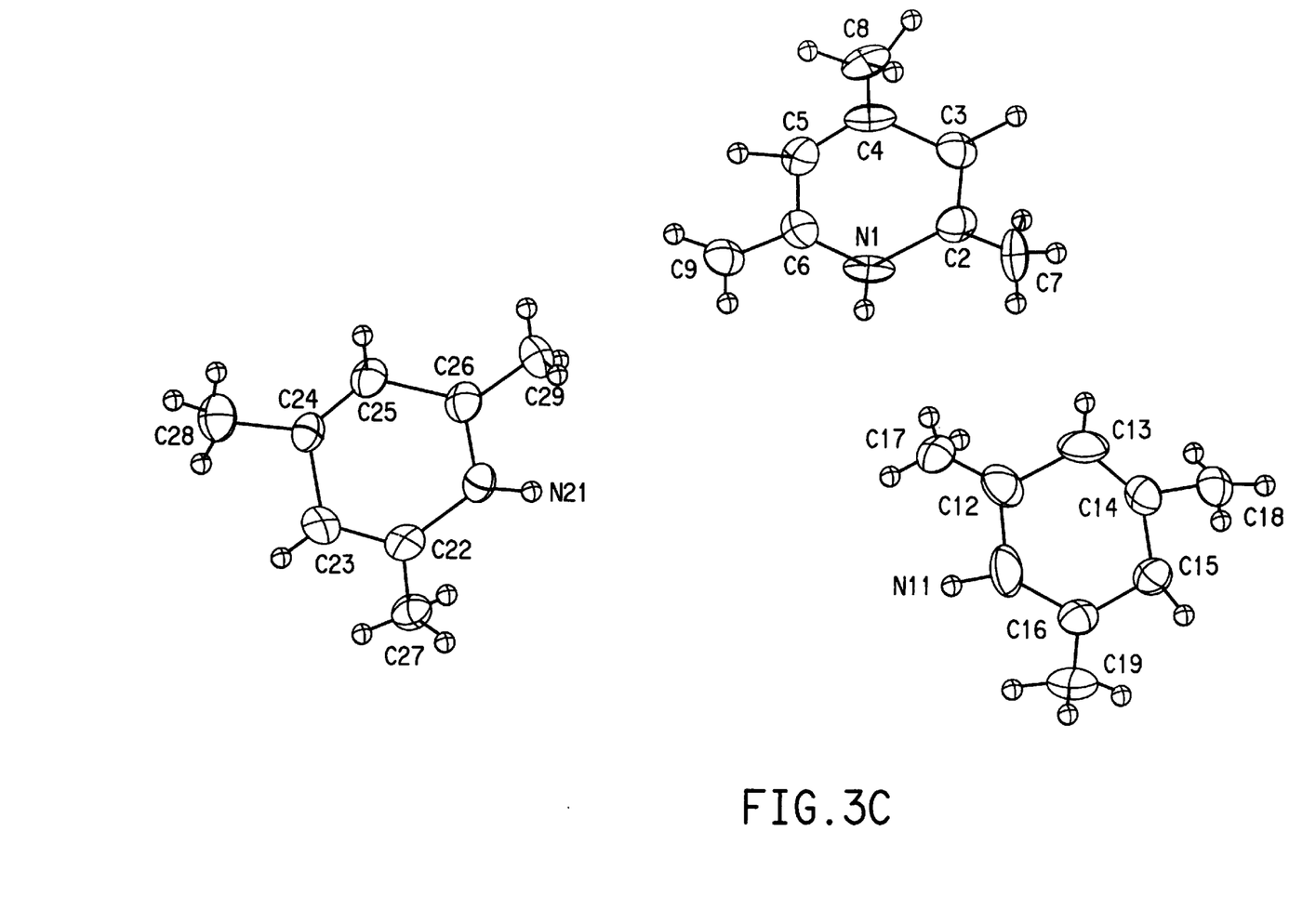
FIG. 3c depicts the structure of collidinium cations as obtained from the x-ray crystal structure of collidinium $AlF_4$.

Inside a nitrogen filled glove box, 10 g of the material pyridineH$^+$ $AlF_4^-$ prepared as in Example 1 was slurried into 50 mL (excess) dry collidine (2,4,6-tri-methylpyridine). This mixture was heated with stirring to 120° C. at which point the white solid completely dissolved to give a pale yellow solution. Stirring was ceased and the solution allowed to slowly cool whereupon colorless needles of the desired compound crystallized from solution as a dense white mat. The solid was collected by filtration and washing with THF then suction dried. Yield=11.5 g (94%). IR (KBr) $AlF_4^-$ at 783 cm$^{-1}$ also AlF species at 687, 629, 603, 520 cm$^{-1}$. $^{27}$Al 51.6 ppm, quintet, J=38 Hz. Solid state $^{19}$F MAS-NMR shows two resonances at −155 ppm (broad) and −187.8 ppm (sharp). A single crystal grown from the above solution in collidine was used for a single crystal structure determination. Crystal data: $AlF_4NC_8H_{12}$ from hot collidine, colorless, needle, 0.05×0.05×0.70 mm, orthorhombic, Pbcn (#60), a 29.673(6), b=16.644(3), c=12.439(3)Å, T=−100° C., V=6143.3Å$^3$, Z=24, FW=225.17, Dc=1.461 g/cc, $\mu$(Mo)= 2.10 cm$^{-1}$. All non-hydrogen atoms refined anisotropic, 526 parameters, data/parameter ratio 6.46, final R=0.044, Rw=0.036, error of fit=1.24. Atomic coordinates are listed in Table III while the structure is depicted in FIG. 3. The structure showed both the tetrahedral $AlF_4^-$ anions (FIG. 3a) and an infinite polymeric chain of octahedral $AlF_6$ units linked through corner and edge sharing of F (FIG. 3b) and stabilized by hydrogen bonded collidinium cations (FIG. 3c).

TABLE III

Fractional Coordinates (X10000) and Isotropic Thermal Parameters

| ATOM | X | Y | Z | BISO |
|---|---|---|---|---|
| Al(1) | 5000 | 5000 | 0 | 1.2(1)' |
| Al(2) | 5000 | 5875(1) | 2500 | 1.1(1)' |
| Al(3) | 5000 | 4137(1) | 2500 | 1.2(1)' |
| Al(4) | 5000 | 10381(1) | 2500 | 3.5(1)' |
| Al(5) | 2339 | 5875(1) | −542(1) | 3.2(1)' |
| F(1) | 4412 | 5006(1) | −146(1) | 1.6(1)' |
| F(2) | 4960(1) | 5802(1) | 1032(1) | 1.4(1)' |
| F(3) | 4954(1) | 4217(1) | 1041(1) | 1.5(1)' |
| F(4) | 4563(1) | 6576(1) | 2566(1) | 1.8(1)' |
| F(5) | 4606(1) | 5008(1) | 2557(1) | 1.3(1)' |
| F(6) | 4565(1) | 3432(1) | 2587(1) | 1.7(1)' |
| F(7) | 5228(1) | 9791(1) | 1581(2) | 6.5(1)' |
| F(8) | 4622(1) | 10964(2) | 1927(2) | 6.0(1)' |
| F(9) | 2061(1) | 5199(1) | −1266(2) | 4.1(1)' |
| F(10) | 1974(1) | 6514(1) | 2(2) | 6.6(1)' |
| F(11) | 2680(1) | 6402(1) | −1325(2) | 4.9(1)' |
| F(12) | 2644(1) | 5430(2) | 383(2) | 6.9(1)' |
| N(1) | 3728(1) | 4431(2) | −1239(2) | 1.7(1)' |
| N(11) | 3874(1) | 7388(2) | 1796(2) | 2.1(1)' |
| N(21) | 4324(1) | 2129(2) | 3709(2) | 2.0(1)' |
| C(2) | 3462(1) | 4813(2) | −1945(3) | 1.9(1)' |
| C(3) | 3062(1) | 4460(2) | −2239(3) | 2.2(1)' |
| C(4) | 2936(1) | 3720(2) | −1819(3) | 2.2(1)' |
| C(5) | 3227(1) | 3349(2) | −1112(3) | 2.2(1)' |
| C(6) | 3626(1) | 3708(2) | −816(3) | 2.0(1)' |
| C(7) | 3610(2) | 5610(3) | −2367(5) | 3.5(1)' |
| C(8) | 2492(2) | 3359(3) | −2124(4) | 3.4(1)' |
| C(9) | 3962(1) | 3342(2) | −76(3) | 2.7(1)' |
| C(12) | 3622(1) | 7042(2) | 1027(3) | 2.1(1)' |
| C(13) | 3229(1) | 7415(2) | 739(3) | 2.5(1)' |
| C(14) | 3090(1) | 8118(2) | 1239(3) | 2.6(1)' |
| C(15) | 3370(1) | 8446(2) | 2009(3) | 2.4(1)' |
| C(16) | 3767(1) | 8078(2) | 2286(3) | 2.3(1)' |
| C(17) | 3793(2) | 6279(3) | 552(4) | 3.1(1)' |
| C(18) | 2646(2) | 8502(4) | 950(5) | 4.5(2)' |
| C(19) | 4083(2) | 8392(4) | 3117(5) | 4.3(2)' |
| C(22) | 4577(1) | 1876(2) | 4542(3) | 2.3(1)' |
| C(23) | 4440(1) | 1199(2) | 5083(3) | 3.0(1)' |
| C(24) | 4051(1) | 795(2) | 4788(3) | 2.6(1)' |
| C(25) | 3809(1) | 1080(2) | 3930(3) | 2.6(1)' |
| C(26) | 3949(1) | 1753(2) | 3372(3) | 2.3(1)' |
| C(27) | 4992(2) | 2340(3) | 4800(4) | 4.0(1)' |
| C(28) | 3916(2) | 43(3) | 5373(4) | 4.3(1)' |
| C(29) | 3721(2) | 2083(3) | 2408(5) | 4.0(1)' |
| H(1N) | 3958(10) | 4639(18) | −1024(23) | 1.5(7) |
| H(3) | 2892(10) | 4704(18) | −2726(23) | 1.9(7) |
| H(5) | 3162(10) | 2863(19) | −760(24) | 1.9(7) |
| H(7) | 3408(18) | 5957(29) | −2513(42) | 8.0(16) |
| H(7') | 3733(16) | 5540(28) | −3034(40) | 7.6(16) |
| H(7") | 3838(15) | 5815(25) | −2097(34) | 5.3(12) |
| H(8) | 2271(14) | 3644(26) | −1878(34) | 5.0(12) |
| H(8') | 2479(14) | 2824(23) | −1891(30) | 4.5(11) |
| H(8") | 2446(13) | 3411(24) | −2885(33) | 4.3(10) |
| H(9) | 4225(15) | 3261(23) | −450(32) | 5.2(11) |
| H(9') | 3860(12) | 2828(21) | 166(27) | 3.4(9) |
| H(9") | 4018(12) | 3693(22) | 550(29) | 3.7(9) |
| H(11N) | 4093(11) | 7169(18) | 1975(25) | 1.5(8) |
| H(13) | 3060(10) | 7177(18) | 206(24) | 1.9(7) |
| H(15) | 3290(12) | 8912(21) | 2358(28) | 3.7(9) |
| H(17) | 3980(16) | 6385(28) | 24(34) | 6.3(14) |
| H(17') | 3562(12) | 5949(22) | 292(28) | 3.4(9) |
| H(17") | 3942(12) | 5963(22) | 1063(30) | 3.7(10) |
| H(18) | 2711(15) | 8899(28) | 521(38) | 5.4(14) |
| H(18') | 2529(17) | 8840(33) | 1444(42) | 7.9(17) |
| H(18") | 2430(23) | 8122(39) | 679(55) | 12.6(24) |
| H(19) | 3941(21) | 8447(36) | 3720(48) | 10.1(23) |
| H(19') | 4203(18) | 8891(32) | 2932(42) | 8.1(16) |
| H(19") | 4283(22) | 8057(36) | 3211(51) | 10.8(23) |
| H(21N) | 4426(12) | 2570(22) | 3345(27) | 3.6(9) |
| H(23) | 4616(12) | 1014(21) | 5637(29) | 3.5(9) |
| H(25) | 3563(10) | 817(18) | 3699(23) | 1.4(6) |
| H(27) | 5154(23) | 2510(43) | 4200(55) | 13.2(28) |
| H(27') | 5182(15) | 2096(26) | 5219(34) | 5.5(13) |
| H(27") | 4911(21) | 2763(36) | 5031(48) | 9.9(20) |
| H(28) | 4162(19) | −374(32) | 5226(39) | 9.1(17) |
| H(28') | 3675(16) | −226(28) | 5081(33) | 6.3(13) |
| H(28") | 3853(18) | 148(33) | 6073(41) | 9.5(18) |
| H(29) | 3490(18) | 2375(30) | 2599(43) | 7.8(16) |
| H(29') | 3594(14) | 1703(25) | 1928(33) | 5.1(12) |
| H(29") | 3917(19) | 2361(33) | 1981(43) | 9.2(18) |

EXAMPLE 4

Preparation of Tetraphenylphosphonium$^+$ AlF$_4^-$

Figures 4A, 4B:
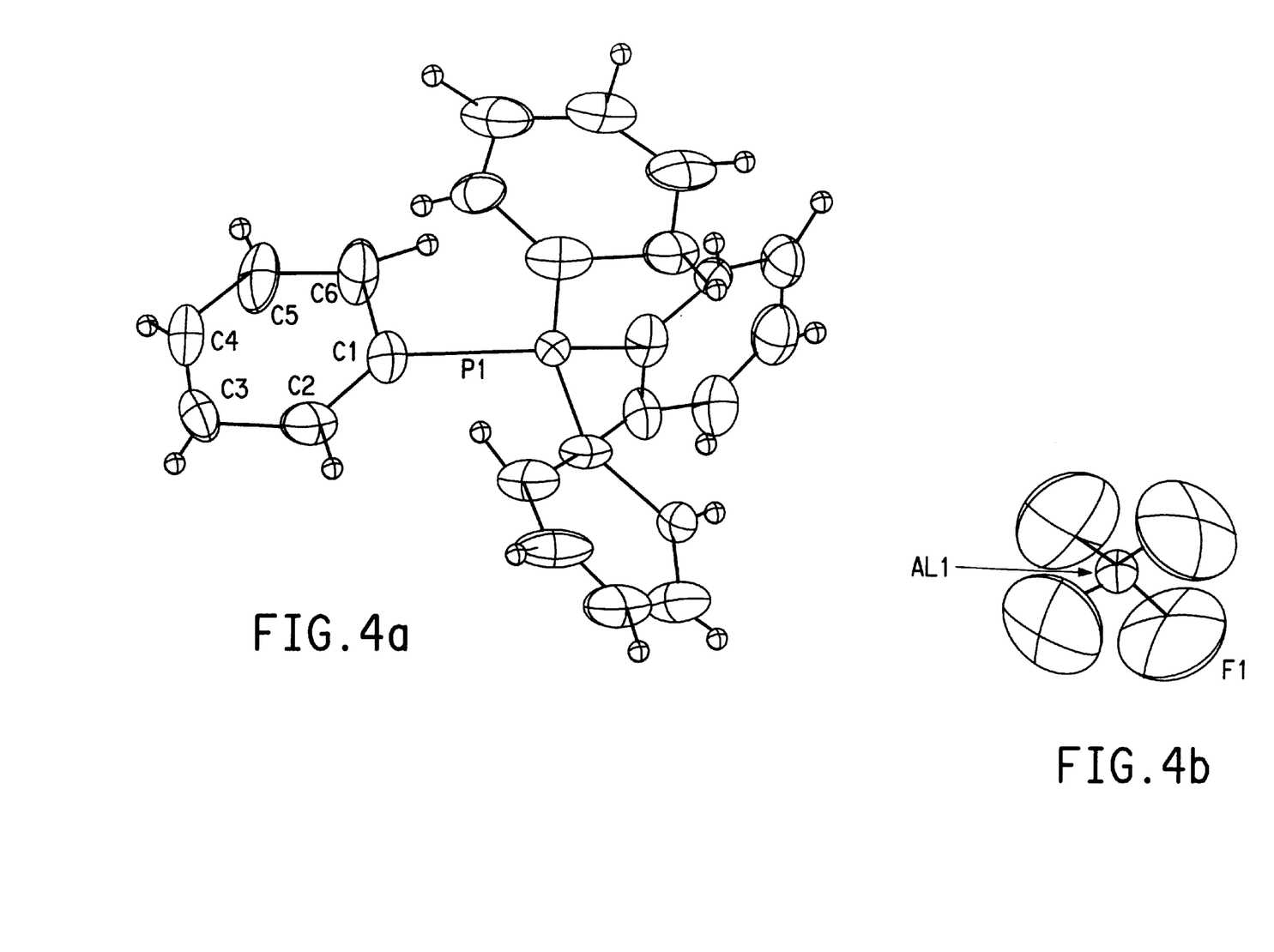
FIG. 4a depicts the structure of the tetrahedral cation $P(C_6H_5)_4^+$ as obtained from the x-ray crystal structure of tetraphenylphosphonium $AlF_4$.
FIG. 4b depicts the structure of the tetrahedral $AlF_4^-$ anion as obtained from the x-ray crystal structure of tetraphenylphosphonium $AlF_4$.

Inside a nitrogen filled glove box, 0.225 g collidine H$^+$ AlF$_4^-$ prepared as in Example 3 was dissolved into 5 mL dry methanol and rapidly mixed with a second solution of 0.42 g tetraphenylphosphonium bromide also in 5 mL methanol. After 30 seconds the clear solution became progressively cloudy and large needle-like crystals of the desired compound began to precipitate from solution. Yield 0.33 g (74%). The material was recrystallized from hot acetone or acetonitrile to give x-ray quality crystals. IR (KBr) AlF$_4^-$ at 787 cm$^{-1}$. NMR (CD$_3$CN): $^{19}$F, −194.6 ppm, 6 lines, J=38 Hz; Solid state $^{19}$F MAS-NMR shows a single sharp resonance at −190 ppm. A single crystal grown from acetonitrile was used for a single crystal structure determination. Crystal data: PAlF$_4$C$_{24}$H$_{20}$ from acetonitrile, colorless, block, 0.26× 0.26×0.50 mm, tetragonal, I$_4$ (#82), a=12.209(3), c=7.050 (2)Å, T=−65° C., V=1050.9Å$^3$, Z=2, FW=442.38, Dc=1.398 g/cc, $\mu$(Mo)=2.09 cm$^-$. All non-hydrogen atoms refined anisotropic, 88 parameters, data/parameter ratio=7.03, final R=0.041, Rw=0.044, error of fit=1.95. Atomic coordinates are listed in Table IV while the structure is depicted in FIG. 4. The structure shows only the two expected tetrahedral ions—the anion AlF$_4^-$ (FIG. 4b) and the cation P(C$_6$H$_5$)$_4^+$ (FIG. 4a).

TABLE IV

Fractional Coordinates (X10000) and Isotropic Thermal Parameters

| ATOM | X | Y | Z | BISO |
|---|---|---|---|---|
| P(1) | 0 | 0 | 0 | 2.3(1)' |
| Al(1) | 0 | 5000 | 2500 | 3.1(1)' |
| F(1) | 356(9) | 4040(5) | 1183(12) | 21.7(4)' |
| C(1) | 978(2) | 669(2) | 1511(4) | 2.6(1)' |
| C(2) | 2094(2) | 458(2) | 1376(4) | 3.1(1)' |
| C(3) | 2807(3) | 984(3) | 2624(6) | 4.0(1)' |
| C(4) | 2413(3) | 1708(3) | 3961(6) | 4.3(1)' |
| C(5) | 1299(3) | 1930(3) | 4065(5) | 4.3(1)' |
| C(6) | 583(2) | 1390(3) | 2855(4) | 3.5(1)' |
| H(2) | 2324(22) | −8(23) | 477(37) | 1.8(5) |
| H(3) | 3653(41) | 747(36) | 2457(90) | 6.6(11) |
| H(4) | 2898(29) | 2109(27) | 4867(64) | 4.6(8) |
| H(5) | 1017(32) | 2384(37) | 4849(90) | 5.6(11) |
| H(6) | −218(29) | 1484(30) | 2771(62) | 4.5(8) |

EXAMPLE 5

Preparation of Tetraphenylarsonium$^+$ AlF$_4^-$

Figure 5A:
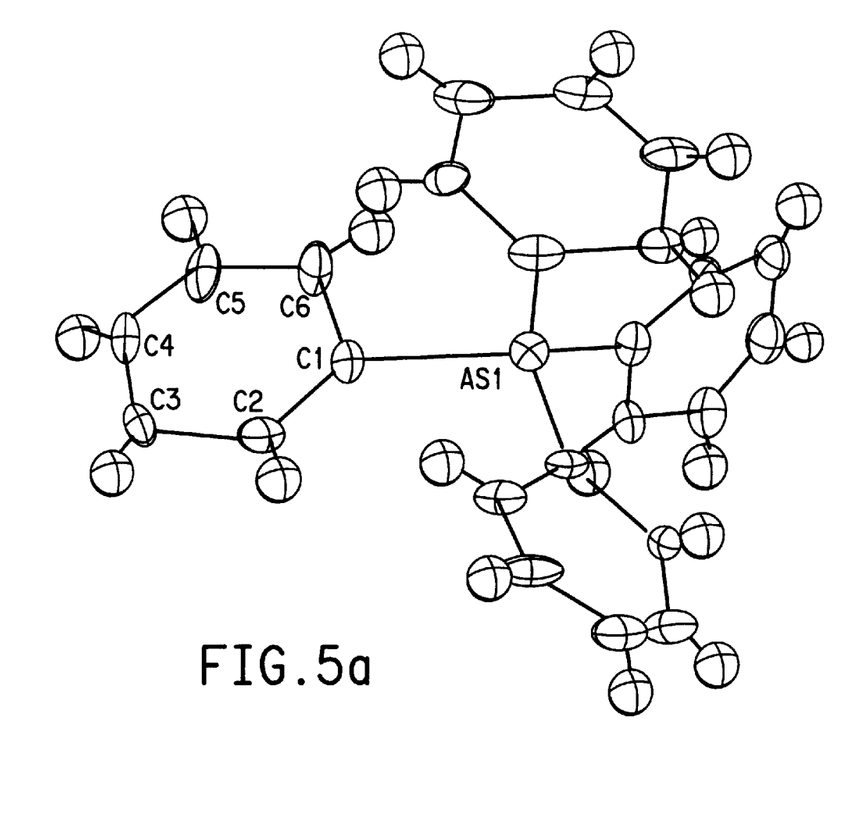
FIG. 5a depicts the structure of the tetrahedral $As(C_6H_5)_4^+$ cation as obtained from the x-ray crystal structure of tetraphenylarsonium $AlF_4$.
Figure 5B:
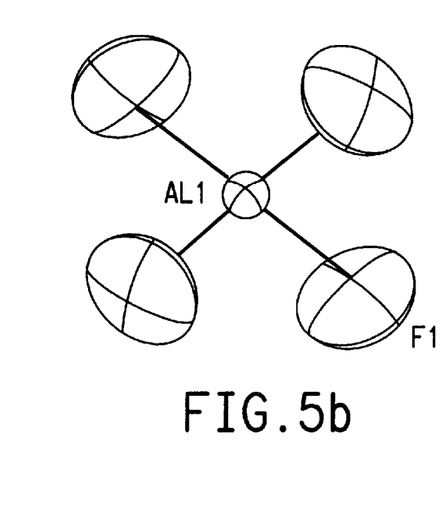
FIG. 5b depicts the structure of the tetrahedral $AlF_4^-$ anion as obtained from the x-ray crystal structure of tetraphenylarsonium $AlF_4$.

Inside a nitrogen filled glove box, 0.225 g collidineH$^+$ AlF$_4^-$ prepared as in Example 3 was dissolved in 5 mL dry methanol and rapidly mixed with a second solution of 0.42 g tetraphenylarsonium chloride also in 5 mL methanol. After 30 seconds the clear solution became progressively cloudy and large needle-like crystals of the desired compound began to precipitate from solution. Yield 0.43 g (88%). The material was recrystallized from hot acetone or acetonitrile to give x-ray quality crystals. IR (KBr) $AlF_4^-$ at 788 cm$^{-1}$, NMR (0.002 M in $CD_3CN$); $^{19}F$, −194.6 ppm, 6 lines, J=38 Hz; Solid state $^{19}F$ MAS-NMR shows a single sharp resonance at −190.1 ppm. A single crystal grown from acetone was used for a single crystal structure determination. Crystal data: $AsAlF_4C_{24}H_{20}$ from acetone, colorless, block. 0.30× 0.26×0.47 mm, tetragonal, $I_4^-$(#82), a=12.466(2), c=6.813 (1)Å, T=−100° C., V=1058.8Å$^3$, Z=2, FW=486.32, Dc=1.525 g/cc, $\mu$ (Mo)=16.82 cm$^{-1}$. All non-hydrogen atoms refined anisotropic, 88 parameters, data/parameter ration=7.78, final R=0.020, Rw=0.023, error of fit 1.24. Atomic coordinates are listed in Table V while the structure is depicted in FIG. 5. The structure shows only the two expected tetrahedral ions—the anion $AlF_4^-$ (FIG. 5b) and the cation $As(C_6H_5)_4^+$ (FIG. 5a).

TABLE V

Fractional Coordinates (X10000) and Isotropic Thermal Parameters

| ATOM | X | Y | Z | BISO |
|---|---|---|---|---|
| As(1) | 0 | 0 | 0 | 1.5(1)' |
| Al(1) | 0 | 5000 | 2500 | 2.2(1)' |
| F(1) | 160(4) | 3953(3) | 1161(6) | 12.4(2)' |
| C(1) | 1016(2) | 713(2) | 1645(3) | 1.8(1)' |
| C(2) | 2102(2) | 454(2) | 1562(3) | 2.2(1)' |
| C(3) | 2808(2) | 972(2) | 2826(4) | 2.8(1)' |
| C(4) | 2439(2) | 1737(2) | 4123(4) | 3.0(1)' |
| C(5) | 1358(2) | 2010(2) | 4174(4) | 3.0(1)' |
| C(6) | 637(2) | 1482(2) | 2952(4) | 2.5(1)' |
| H(2) | 2338(24) | −21(23) | 797(43) | 2.2(5) |
| H(3) | 3595(28) | 652(29) | 2673(61) | 3.5(7) |
| H(4) | 2871(24) | 2138(22) | 5247(66) | 3.2(6) |
| H(5) | 1057(25) | 2548(25) | 4928(95) | 3.9(6) |
| H(6) | −139(25) | 1729(24) | 2957(42) | 2.4(6) |

EXAMPLE 6

Preparation of Tetraethylphosphonium$^+$ $AlF_4^-$

A mixture of 0.45 g $PEt_4^+Br^-$ in 10 ml dry THF was treated with 0.42 g of $KN(SiMe_3)_2$ (Commercial, Aldrich) in a nitrogen atmosphere and was stirred 3 hours at room temperature. The resulting mixture was filtered, obtaining 0.24 g off-white solid which was discarded (theoretical yield of KBr, ca. 0.24 g). The solution was added to a suspension of 0.35 g pyridineH$^+$ $AlF_4^-$ in 10 ml dry pyridine in a nitrogen atmosphere and the mixture was stirred, soon becoming a pale yellow solution. After ca. 30 min the solution was evaporated to dryness and the residue recrystallized twice from $CH_2Cl_2$, yield 0.12 g. IR (Nujol) 786 cm$^{-1}$, $^1H$ NMR ($CD_3CN$): 1.16 ppm, d (18 Hz) of t (8 Hz); 2.10 ppm, d (13 Hz) of q (8 Hz) $^{19}F$ NMR ($CD_3CN$): −193 ppm, 6 lines, J=38 Hz, $^{27}Al$ NMR ($CD_3CN$): quintet, J=38 Hz. C. H. anal. Calcd. C: 38.41, H: 8.06%. Found C: 37.83, 38.27; H: 8.11, 8.15%.

The reaction between $P(C_2H_5)_4^+Br^-$ and $KN(Si(CH_3)_3)_2$ in THF is well known to form KBr, the amine $HN(Si(CH_3)_3)_2$, and the ylid $(C_2H_5)_3P=CHCH_3$, and the ylid was not isolated for this Example.

In a related preparation, 0.55 g $P(C_2H_5)_4^+Br^-$ and 0.48 g $KN(Si(CH_3)_3)_2$ were stirred in 15 ml dry THF for 30 min, the mixture was filtered, and the solution added to 0.47 g pyridineH$^+AlF_4^-$ in 10 ml pyridine, all in a nitrogen atmosphere. After stirring for several minutes the mixture became a solution which was evaporated; the residue was recrystallized from $CH_2Cl_2$/ether, yield 0.41 g (68%). IR, $^1H$ and $^{19}F$ NMR as above.

EXAMPLE 7

Preparation of Triphenylmethylphosphonium$^+AlF_4^-$

Figure 6:
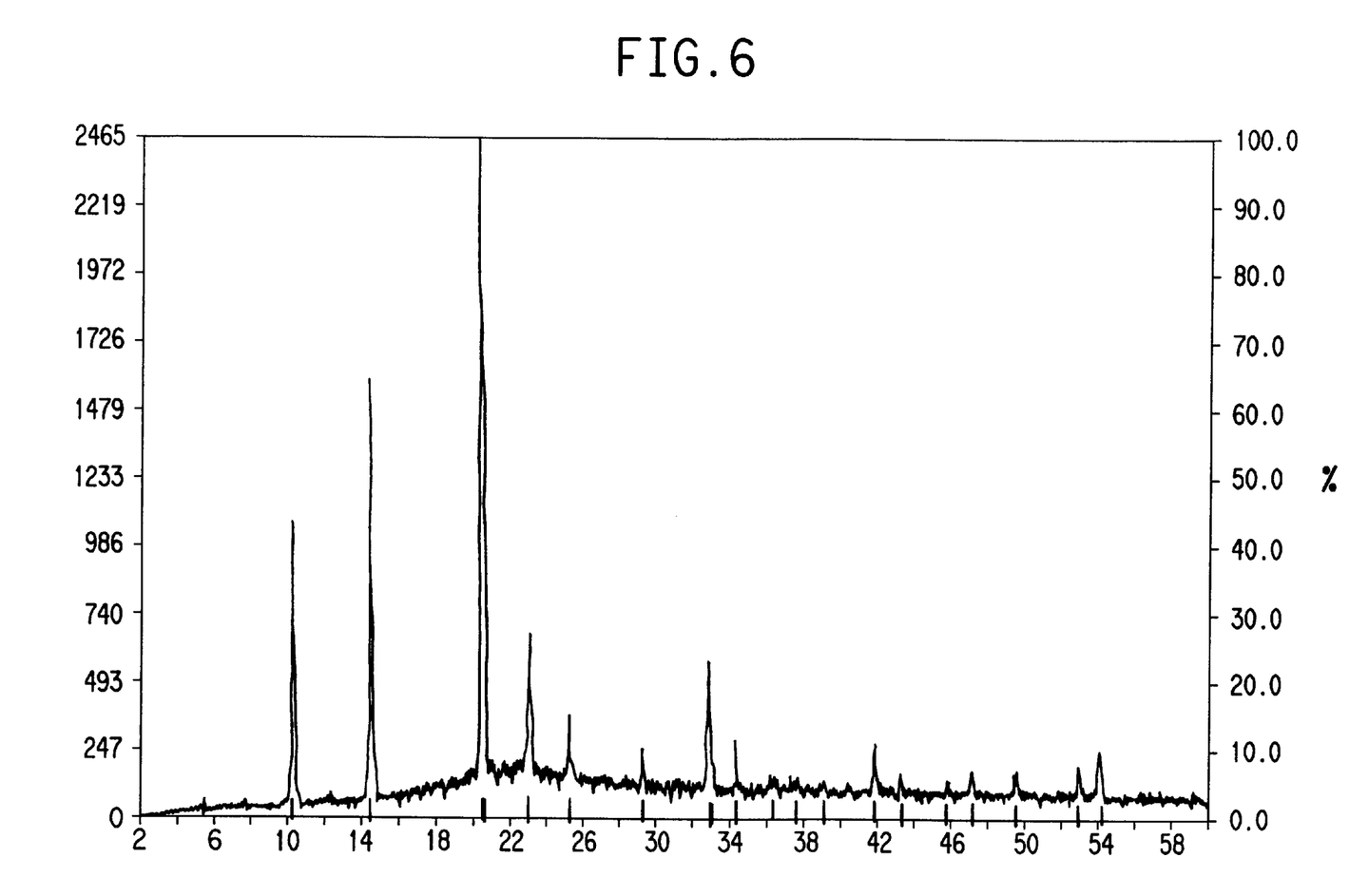
FIG. 6 depicts the powder X-ray diffraction pattern of $M^{+n}(AlF_4^-)_n$ wherein $M^{+n}$ is the triphenylmethylphosphonium cation and n is 1.

Inside a nitrogen filled glove box, 0.225 g collidineH$^+$ $AlF_4^-$ prepared as in Example 3 was dissolved into 5 mL dry methanol and rapidly mixed with a second solution of 0.36 g triphenylmethylphosphonium bromide also in 5 mL methanol. The clear solution was evaporated to dryness and the white powder was extracted into acetone leaving behind collidinium bromide which was removed by filtration. The clear acetone solution was evaporated to dryness forming colorless needle-shaped crystals of the desired material. Yield 0.23 g (61%). Thermal analysis of the crystals showed a single, sharp, weight loss event centered at 495° C. and a weight change corresponding exactly to the transformation to $AlF_3$. X-ray powder diffraction data are listed in Table VI and depicted in FIG. 6.

TABLE VI

| Generator settings | 40 kv, 30 mA |
|---|---|
| CU alpha1, 2 wavelengths | 1.540598, 1.544435 Ang |
| Step size, sample time | 0.020 deg, 0.50 s, 25.00 s/deg |
| Monochromator used | Yes |
| Divergence slit | Automatic (specimen length: 12.5 mm) |
| Peak angle range | 2.000–60.000 deg |
| Peak position criterion | Centroid second derivative |
| Number of peaks in file | 24 (Alpha1: 21, Amorphous: 0) |

| Peak No. | Angle (deg) | Width (deg) | Peak (cts) | Backg (cts) | D spac (Ang) | I/Imax (%) | Type A1 | A2 |
|---|---|---|---|---|---|---|---|---|
| 1 | 5.290 | 1.92 | 10 | 6 | 16.7059 | 0 | X | X |
| 2 | 10.145 | 0.16 | 961 | 27 | 8.7194 | 44 | X | X |
| 3 | 14.408 | 0.12 | 1332 | 40 | 6.1479 | 61 | X | X |
| 4 | 20.417 | 0.10 | 2200 | 95 | 4.3498 | 100 | X | X |
| 5 | 20.532 | 0.10 | 1406 | 95 | 4.3257 | 64 | X | X |
| 6 | 22.930 | 0.18 | 529 | 99 | 3.8786 | 24 | X | X |
| 7 | 25.105 | 0.10 | 250 | 103 | 3.5472 | 11 | X | X |
| 8 | 29.117 | 0.08 | 130 | 111 | 3.0669 | 6 | X | X |
| 9 | 32.635 | 0.08 | 350 | 97 | 2.7417 | 16 | X | |
| 10 | 32.728 | 0.08 | 454 | 97 | 2.7364 | 21 | X | X |
| 11 | 32.865 | 0.04 | 182 | 97 | 2.7298 | 8 | | X |
| 12 | 34.145 | 0.06 | 144 | 95 | 2.6238 | 7 | X | |
| 13 | 34.268 | 0.06 | 76 | 93 | 2.6212 | 3 | | X |
| 14 | 36.230 | 0.40 | 30 | 89 | 2.4795 | 1 | X | X |
| 15 | 37.475 | 0.12 | 42 | 91 | 2.3999 | 2 | X | X |
| 16 | 38.952 | 0.20 | 24 | 89 | 2.3122 | 1 | X | X |
| 17 | 41.688 | 0.06 | 151 | 84 | 2.1666 | 7 | X | X |
| 18 | 43.118 | 0.06 | 59 | 86 | 2.0980 | 3 | X | X |
| 19 | 45.548 | 0.24 | 21 | 84 | 1.9916 | 1 | X | X |
| 20 | 46.967 | 0.24 | 81 | 82 | 1.9347 | 4 | X | X |
| 21 | 49.315 | 0.24 | 64 | 78 | 1.8479 | 3 | X | X |
| 22 | 52.803 | 0.14 | 88 | 75 | 1.7338 | 4 | X | X |
| 23 | 53.993 | 0.10 | 177 | 68 | 1.6969 | 8 | X | |
| 24 | 54.143 | 0.06 | 102 | 68 | 1.6968 | 5 | | X |

EXAMPLE 8

Preparation of Tetraethylammonium$^+$ $AlF_4^-$

Figure 7:
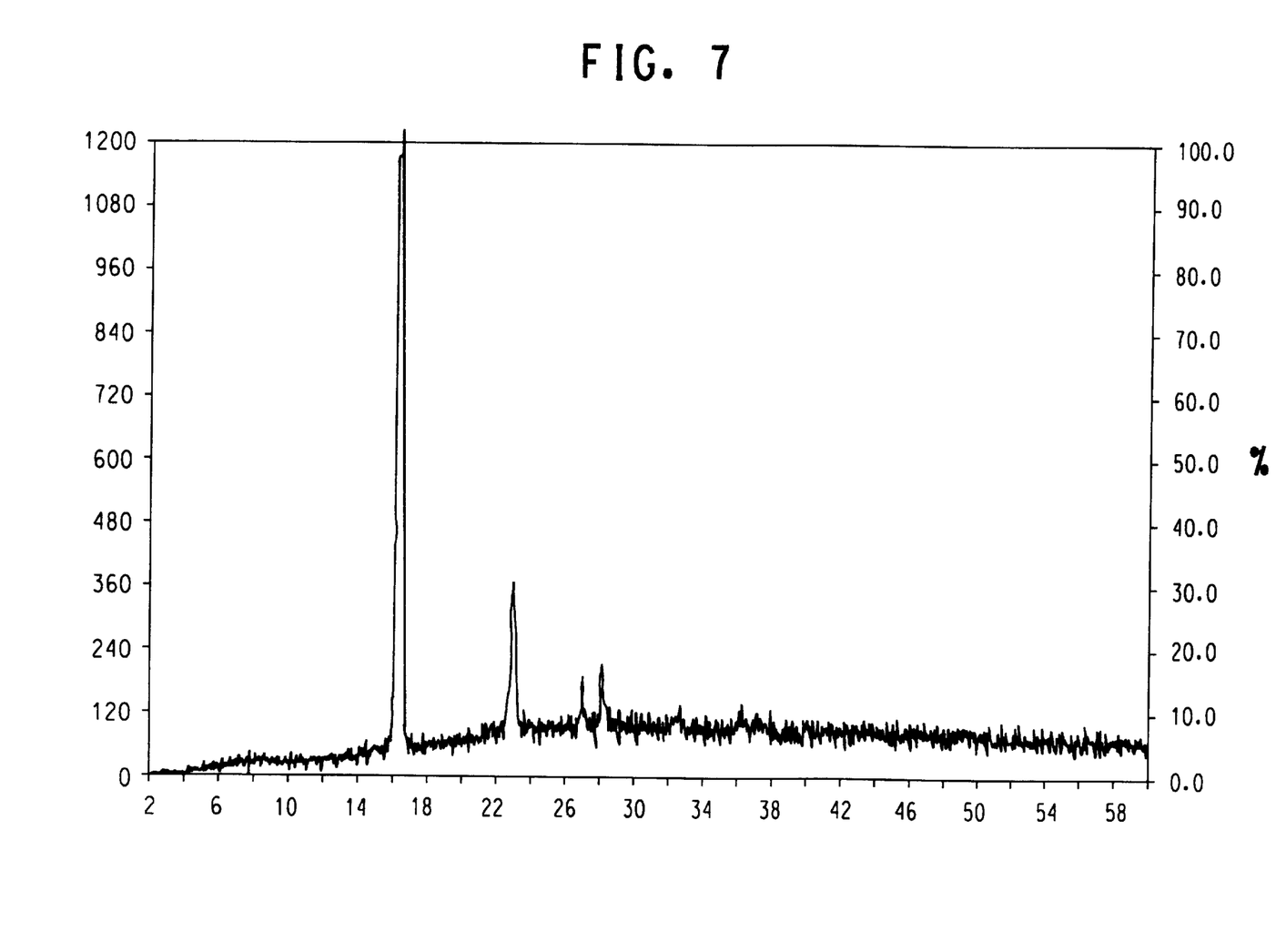
FIG. 7 depicts the powder X-ray diffraction pattern of Mn+(AlF4−) wherein Mn+ is the tetraethylammonium cation and n is 1.

Inside a nitrogen filled glove box, 0.90 g collidineH$^+$ $AlF_4^-$ prepared as in Example 3 was dissolved in 10 mL warm methanol and then mixed with a second solution containing 0.66 g tetraethylammonium chloride dissolved in 10 mL methanol. After stirring for 15 mins the clear solution was evaporated to dryness and the white solid was placed in a horizontal tube furnace. The solid was heated to 300° C. in flowing nitrogen (50 cc/min) at 10° C. min and then held at 300° C. for 30 mins before cooling in nitrogen. The sample was then returned to the glove box and the solid was extracted into dry acetonitrile. The clear acetonitrile was evaporated to dryness leaving hygroscopic, clear, blocky crystals of the desired material. Yield 0.46 g (49%). Thermal analysis of these crystals shows a single, sharp, weight loss event centered at 400° C. and a weight change corresponding exactly to the transformation to AlF$_3$. X-ray powder diffraction data are listed in Table VII and depicted in FIG. 7. $^{19}$F NMR (0.002 M in CD$_3$CN): $^{19}$F, −194.6 ppm, 6 lines, J=38 Hz.

TABLE VII

| Generator settings | 40 kv, 30 mA |
|---|---|
| CU alpha1, 2 wavelengths | 1.540598, 1.544435 Ang |
| Step size, sample time | 0.020 deg, 0.50 s, 25.00 s/deg |
| Monochromator used | Yes |
| Divergence slit | Automatic (specimen length: 12.5 mm) |
| Peak angle range | 2.000–60.000 deg |
| Peak position criterion | Centroid second derivative |
| Number of peaks in file | 11 (Alpha1: 11, Amorphous: 0) |

| Peak No. | Angle (deg) | Width (deg) | Peak (cts) | Backg (cts) | D spac (Ang) | I/Imax (%) | Type A1 | Type A2 |
|---|---|---|---|---|---|---|---|---|
| 1 | 7.715 | 1.92 | 10 | 11 | 11.4595 | 1 | X | X |
| 2 | 16.077 | 0.06 | 1076 | 33 | 5.5129 | 97 | X | X |
| 3 | 16.225 | 0.06 | 1076 | 33 | 5.4631 | 97 | X | X |
| 4 | 16.332 | 0.06 | 1116 | 35 | 5.4274 | 100 | X | X |
| 5 | 16.460 | 0.04 | 595 | 35 | 5.3856 | 54 | X | X |
| 6 | 22.982 | 0.24 | 272 | 62 | 3.8698 | 24 | X | X |
| 7 | 26.995 | 0.12 | 69 | 82 | 3.3030 | 6 | X | X |
| 8 | 28.100 | 0.24 | 102 | 82 | 3.1756 | 9 | X | X |
| 9 | 32.585 | 0.96 | 10 | 89 | 2.7480 | 1 | X | X |
| 10 | 36.285 | 0.56 | 30 | 75 | 2.4759 | 3 | X | X |
| 11 | 49.553 | 0.96 | 10 | 66 | 1.8396 | 1 | X | X |

What is claimed is:

1. A process for the preparation of $M^{+n}(AlF_4^-)_n$ wherein $M^{+n}$ is selected from the group consisting of $N(R_2)_4$, $P(R_2)_4$, $As(R_2)_4$, $HN(R_2)_3$, $H_2N(R_2)_2$, $H_3N(R_2)$, $(R_2)_3P=N=P(R_2)_3$, $S[N(R_2)_2]_3$, R is hydrogen, $C_1$–$C_{10}$ linear or branched alkyl or aryl;

$R_2$ is $C_1$–$C_{10}$ linear or branched alkyl or aryl;

n is 1 to 3 k is 1 to 10;

provided that $M^{+n}$ is other than $NMe_4^+$, $NEt_4^+$, $N(n-Bu)_4^+$, guanidinium $(H_2N=C(NH_2)_2)^+$ and pyridinium $(C_5H_6N)_3^+$ comprising reacting $Al(R)_3$ with $M^{+n}(HF)_qF_n$ wherein $M^{+n}$ is an organic cation or polycation other than $H^+$;

n is an integer from 1 to 3;

q is an integer of at least 1;

and each R is independently alkyl, alkoxy, enolate, aryl, or alkamide.

2. A process for the preparation of $M^{+n}(AlF_4^-)_n$ wherein $M^{+n}$ is of formula $ZH_n^{+n}$ and Z is a base capable of accepting n protons wherein n is an integer of 1 to 3, comprising reacting $Al(R)_3$ wherein each R is independently alkyl, alkoxy, enolate, aryl, or alkamide with a solution of HF and Z.

3. A process for the preparation of $M^{+n}(AlF_4^-)_n$ wherein $M^{+n}$ is as defined in claim 1, and n is an integer from 1 to 3 comprising reacting $ZH_m^{+m}$ $(AlF_4^-)_m$ and Y wherein Z is a base capable of accepting m protons wherein m is an integer of 1 to 3, and Y is a base capable of accepting n protons or a phosphorus ylid of formula $R_1R_2R_3P=CR_4R_5$ wherein $R_1$, $R_2$ and $R_3$ are each independently linear, branched or cyclic alkyl or substituted alkyl, alkylene, alkoxy, aryl, aryloxy, heterocyclic, substituted heterocyclic, or together two or more of $R_1$, $R_2$ or $R_3$ may form a ring;

$R_4$ and $R_5$ are each independently hydrogen, linear, branched or cyclic alkyl or substituted alkyl, alkylene, alkoxy, aryl, aryloxy, heterocyclic, substituted heterocyclic or $R_4$ and $R_5$ together may form a ring; and Y is a stronger base than Z.

4. A process for the preparation of $M^{+n}(AlF_4^-)_n$ wherein $M^{+n}$ is as defined in claim 1, and n is an integer from 1 to 3 comprising reacting $ZH_m^{+m}(AlF_4^-)_m$ wherein Z is a base capable of accepting m protons wherein m is an integer from 1 to 3, with $M^{+n}(X^-)_n$ wherein $M^{+n}$ is an organic cation or polycation other than $H^+$ and $X^-$ is a stronger base than Z.

5. A process for the preparation of $M^{+n}(AlF_4^-)_n$ wherein $M^{+n}$ is as defined in claim 1 or 3, and n is an integer from 1 to 3 comprising reacting $ZH_m^{+m}(AlF_4^-)_m$ wherein Z is a base capable of accepting m protons wherein m is an integer of 1 to 3, with $M^{+n}(X^-)_n$ wherein $M^{+n}$ is an organic cation or polycation other than $H^+$ and $X^-$ is an anion which forms a compound $ZE_m^{+m}(X^-)_m$ easily separable from the $M^{+n}(AlF_4^-)_n$ product.

* * * * *